(12) United States Patent
Jayasena et al.

(10) Patent No.: US 6,531,286 B2
(45) Date of Patent: *Mar. 11, 2003

(54) HOMOGENEOUS DETECTION OF A TARGET THROUGH NUCLEIC ACID LIGAND-LIGAND BEACON INTERACTION

(75) Inventors: Sumedha Jayasena, Boulder, CO (US); Larry Gold, Boulder, CO (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/907,074

(22) Filed: Jul. 17, 2001

(65) Prior Publication Data

US 2001/0055773 A1 Dec. 27, 2001

Related U.S. Application Data

(63) Continuation of application No. 09/581,326, filed as application No. PCT/US98/26599 on Aug. 11, 2000, now Pat. No. 6,261,783, which is a continuation of application No. 09/157,206, filed on Sep. 18, 1998, now Pat. No. 5,989,823.
(60) Provisional application No. 60/068,135, filed on Dec. 15, 1997.

(51) Int. Cl.[7] .......................... C12Q 1/68; G01N 33/53
(52) U.S. Cl. .................................. 435/6; 435/7.1; 436/94
(58) Field of Search .......................... 435/6, 7.1; 436/94

(56) References Cited

U.S. PATENT DOCUMENTS

| 4,801,530 A | 1/1989 | Nogueira et al. |
| 4,894,325 A | 1/1990 | Englehardt et al. |
| 5,118,801 A | 6/1992 | Lizardi et al. |
| 5,270,163 A | 12/1993 | Gold et al. |
| 5,288,609 A | 2/1994 | Englehardt et al. |
| 5,312,728 A | 5/1994 | Lizardi et al. |
| 5,487,973 A | 1/1996 | Nilsen et al. |
| 5,691,145 A | 11/1997 | Pitner et al. |
| 5,723,323 A | 3/1998 | Kauffman et al. |
| 5,849,489 A | 12/1998 | Heller |
| 5,989,823 A | 11/1999 | Jayasena et al. |

FOREIGN PATENT DOCUMENTS

| GB | 2 183 661 A | 6/1987 |
| WO | WO 89/06694 | 7/1989 |
| WO | WO 91/19813 | 12/1991 |
| WO | WO 92/14843 | 9/1992 |
| WO | WO 97/09342 | 3/1997 |
| WO | WO 97/42345 | 11/1997 |
| WO | WO98/04740 | 2/1998 |

OTHER PUBLICATIONS

Ellington & Szostak (1990) Abstracts of papers presented at the 1990 meeting on RNA Processing, Cold Spring Harbor Laboratory, Cold Spring Harbor, NY, p. 84.
Joyce (1989) Gene 82:83–87.
Joyce & Inoue (1989) Nucleic Acids Research 17:711–722.
Kinzler & Vogelstein (1989) Nucleic Acids Research 17:3645–3652.

(List continued on next page.)

*Primary Examiner*—Kenneth R. Horlick

(57) ABSTRACT

A homogeneous assay that utilizes molecular beacons as the reporter and nucleic acid ligands as the sensor is described. This assay, called the ligand beacon assay, is for the detection of target molecules in a test mixture. The concept of the ligand beacon assay was tested using several proteins to which high affinity and specific nucleic acid ligands are available. The assay specifically detects the molecular target that binds the nucleic acid ligand with high affinity and specificity. The range of the assay is dictated by the concentration of the nucleic acid ligand/ligand beacon pair used in the assay. Target proteins were detected in buffer as well as in plasma, expanding its applicability to clinical use. This is a simple to use and fast assay format with the potential for automation for high throughput screening applications.

10 Claims, 19 Drawing Sheets

OTHER PUBLICATIONS

Kostrikis et al. (1998) Science 279:1228–1229.
Kramer et al. (1974) J. Mol. Biol. 89:719–736.
Levisohn & Spiegelman (1969) Proc. Natl. Acad. Sci. USA 63:805–811.
Levisohn & Spiegelman (1968) Proc. Natl. Acad. Sci. USA 60:866–872.
Nyren et al. (1992) Analytical Biochem. 208:171–175.
Oliphant et al. (1989) Mol. Cell. Biol. 9:2944–2949.
Oliphant & Struhl (1988) Nucleic Acids Research 16:7673–7683.
Oliphant & Struhl (1987) Methods in Enzymology 155:568–583.
Oliphant et al. (1986) Gene 44:177–183.
Robertson & Joyce (1990) Nature 344:467–468.
Thiesen & Bach (1990) Nucleic Acids Research 18:3203–3208.
Tyagi et al. (1998) Nature Biotechnology 16:49–53.
Tyagi et al. (1996) Nature Biotechnology 14:303–308.

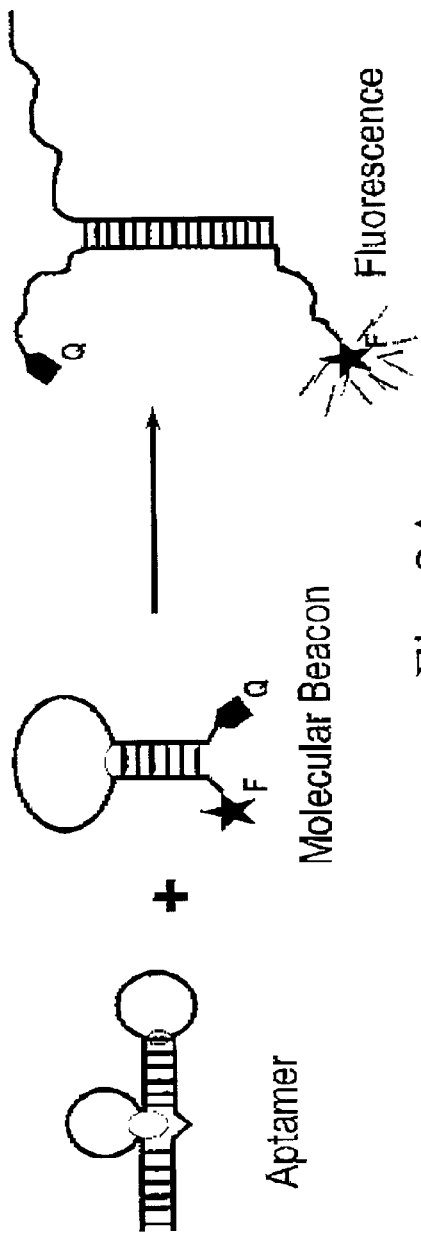
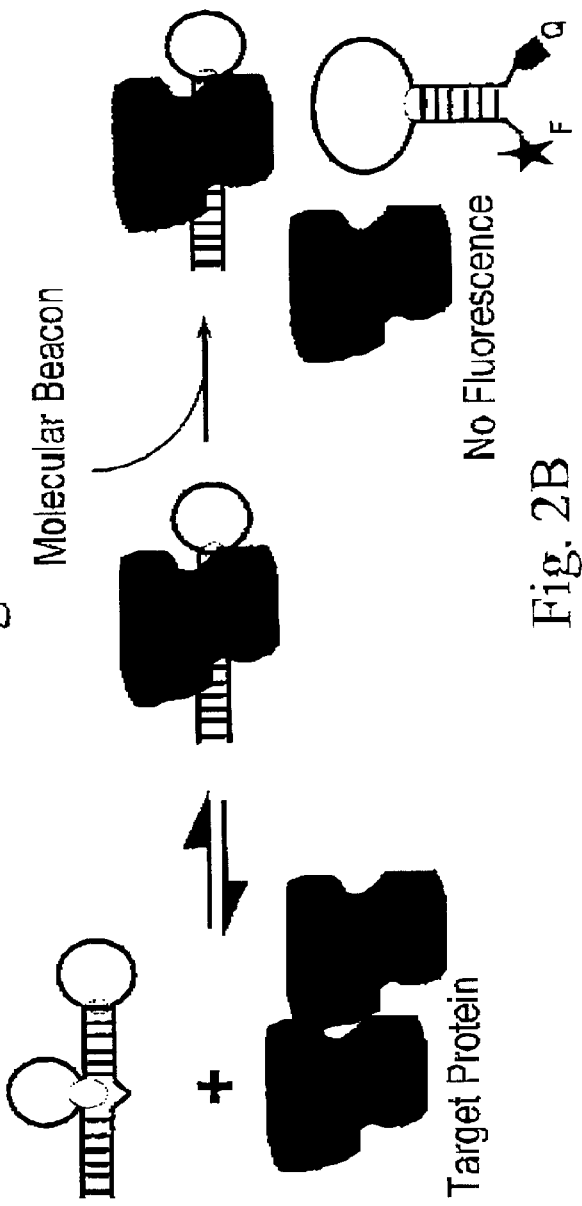
Fig. 2A
Fig. 2B

Taq Ligand Beacon: 5'-FGCGAGCAAGAACAAAACGCTAAGAATGCTCTCGCQ-3'
SEQ ID NO:4

PDGF Ligand Beacon: 5'-FGCGAGAAAAGTAACCACGAAGAACGGCCCCTCGCQ-3'
SEQ ID NO:2

L-Selectin Ligand Beacon: 5'-FGCGAGTGTACTGGTTACCTTGGCTACTCGCQ-3'
SEQ ID NO:6

P-Selectin Ligand Beacon: 5'-FGCGAGCTCGGCGTTTGCTGAGCTCGACTCGCQ-3'
SEQ ID NO:8

Fig. 3B

Quenched Fluorophores

Stem-loop I    A 5' AGGCTAGCTA⟶ PROBE
               B 3' TTAGAGGGAT⟶

Stem-loop II    B' 5' AATCTCCCTA ⟶
               C 3' GGAGTTTGAT ⟶

Stem-loop III    C' 5' CCTCAAACTA ⟶
               A' 3' TCCGATCGAT ⟶

Fig. 14A

C' 5' CCTCAAACTA ⟶
A' 3' TCCGATCGAT ⟶

A 5' AGGCTAGCTA⟶
B 3' TTAGAGGGAT⟶    Target

B' 5' AATCTCCCTA ⟶
C 3' GGAGTTTGAT ⟶

Fig. 14B

C' 5' CCTCAAACTA ⟶
A' 3' TCCGATCGAT ⟶
A 5' AGGCTAGCTA⟶
B 3' TTAGAGGGAT ⟶    Target
B' 5' AATCTCCCTA ⟶
C 3' GGAGTTTGAT ⟶

Fig. 14C

B' 5' AATCTCCCTA ⟶
C 3' GGAGTTTGAT ⟶
C' 5' CCTCAAACTA ⟶
A' 3' TCCGATCGAT ⟶
A 5' AGGCTAGCTA ⟶
B 3' TTAGAGGGAT ⟶
B' 5' AATCTCCCTA ⟶    Target
C 3' GGAGTTTGAT ⟶
C' 5' CCTCAAACTA ⟶
A' 3' TCCGATCGAT ⟶

Fig. 14D

HOMOGENEOUS DETECTION OF A TARGET THROUGH NUCLEIC ACID LIGAND-LIGAND BEACON INTERACTION

RELATED APPLICATIONS

This application is a continuation of U.S. application Ser. No. 09/581,326, filed Aug. 11, 2000, now U.S. Pat. No. 6,261,783, which is a 371 of PCT/US98/26599, filed Dec. 15, 1998, each entitled, "Homogeneous Detection of a Target Through Nucleic Acid Ligand-Ligand Beacon Interaction." PCT/US98/26599 claims the benefit of U.S. Provisional Application Serial No. 60/068,135, filed Dec. 15, 1997, entitled "System for Amplifying Fluorescent Signal Through Hybridization Cascade" and is a continuation in part of U.S. application Ser. No. 09/157,206, filed Sep. 18, 1998, entitled "Homogeneous Detection of a Target Through Nucleic Acid Ligand-Ligand Beacon Interaction," now U.S. Pat. No. 5,989,823.

FIELD OF THE INVENTION

This invention is directed to novel methods for the highly selective detection of specific target molecules. In one embodiment the methods described can be used to detect exceedingly low concentrations of said target molecules by virtue of a highly efficient signal amplification mechanism. In another embodiment the binding of a nucleic acid ligand to a target molecule is accompanied by a change in the fluorescence spectrum of the assay solution. The subject invention will be useful in any application where it is desired to detect a target molecule.

BACKGROUND OF THE INVENTION

Techniques that allow specific detection of target molecules or analytes are important for many areas of research, as well as for clinical diagnostics. Central to most detection techniques are ligands that dictate specific and high affinity binding to a target molecule of interest. In immunodiagnostic assays antibodies mediate specific and high affinity binding, whereas in assays detecting nucleic acid target sequences, complementary oligonucleotide probes fulfill this role. To date, antibodies have been able to provide molecular recognition needs for a wide variety of target molecules and have been the popular choice of the class of ligands for developing diagnostic assays.

Recently, a novel class of oligonucleotide probes, referred to as molecular beacons, that facilitate homogeneous detection of specific nucleic acid target sequences has been described (Piatek et al. (1998) Nature Biotechnology 16:359–363; Tyagi and Kramer (1996) Nature Biotechnology 14:303–308). Molecular beacons are nucleic acid sequences that contain a fluorophore and a quencher (FIG. 1; star and filled circle, respectively). By design, molecular beacons are expected to fold into stem-loop structures in which the fluorophore is placed in close proximity to the quencher. When the molecular beacon is illuminated with light corresponding to the excitation wavelength of the fluorescent group, no fluorescence is observed, because energy transfer occurs between the fluorescent group and the quenching group, such that light emitted from the fluorescent group upon excitation is absorbed by the quenching group.

The loop region of molecular beacons is designed to contain a nucleotide sequence complementary to the target sequence of interest. When the molecular beacon is contacted with sequences complementary to the loop, the loop hybridizes to this sequence. This process is energetically favored as the intermolecular duplex formed is longer, and therefore more stable, than the intramolecular duplex formed in the stem region. As this intermolecular double helix forms, torsional forces are generated that cause the stem region to unwind. As a result, the fluorescent group and the quenching group become spatially separated such that the quenching group is no longer able to efficiently absorb light emitted from the fluorescent group. Thus, binding of the molecular beacon to its target nucleic acid sequence is accompanied by an increase in fluorescence emission from the fluorescent group. Molecular beacons undergo intermolecular hybridization upon interaction with the specific target sequence. Molecular beacons have been used for homogeneous detection of specific nucleic acid sequences, both DNA and RNA (Leone et al. (1998) Nucleic Acids Research 26:2150–2155; Piatek et al. (1998) Nature Biotechnol. 16:359–363; Tyagi and Kramer (1996) Nature Biotecnol. 14:303–308).

It is possible to simultaneously use two or more molecular beacons with different sequence specificities in the same assay. In order to do this, each molecular beacon is labeled with at least a different fluorescent group. The assay is then monitored for the spectral changes characteristic for the binding of each particular molecular beacon to its complementary sequence. In this way, molecular beacons have been used to determine whether an individual is homozygous wild-type, homozygous mutant or heterozygous for a particular mutation. For example, using one quenched-fluorescein molecular beacon that recognizes the wild-type sequence and another rhodamine-quenched molecular beacon that recognizes a mutant allele, it is possible to genotype individuals for the β-chemokine receptor (Kostrikis et al. (1998) Science 279:1228–1229). The presence of only a fluorescein signal indicates that the individual is wild-type, and the presence of rhodamine signal only indicates that the individual is a homozygous mutant. The presence of both rhodamine and fluorescein signal is diagnostic of a heterozygote. Tyagi and coworkers have even described the simultaneous use of four differently labeled molecular beacons for allele discrimination. (Tyagi et al. (1998) Nature Biotechnology 16:49–53).

Although useful for the detection of nucleic acid targets, molecular beacons have not been used for detecting other types of molecules. Indeed, there has been no suggestion made in the art that molecular beacons can be used for anything other than detecting specific nucleic acids in mixtures containing a plurality of nucleic acids. Detection of nucleic acids is undeniably important, but in many applications—especially medical diagnostic scenarios— detection of non-nucleic acid molecules, such as proteins, sugars, and small metabolites, is required.

In general, the detection of non-nucleic acid target molecules is a more complicated matter than the detection of nucleic acids, and no single method is universally applicable. Specific proteins may be detected through the use of antibody-based assays, such as an enzyme linked immunoassay (ELISA). In one form of ELISA, a primary antibody binds to the protein of interest, and signal amplification is achieved using a labeled secondary antibody that can bind to multiple sites on the primary antibody. This technique can only be used to detect molecules for which specific antibodies exist. The generation of new antibodies is a time consuming and very expensive procedure and many proteins are not sufficiently immunogenic to generate antibodies in host animals. Furthermore, it is often necessary to measure and detect small molecules, such as hormones and sugars, that are generally not amenable to antibody recognition. In these cases, enzymatic assays for the specific molecule are often required.

The discovery of the SELEX™ (Systematic Evolution of Ligands by EXponential enrichment) process enables the identification of nucleic acid-based ligands, referred to as aptamers, that recognize molecules other than nucleic acids with high affinity and specificity (Ellington and Szostak (1990) Nature 346:818–822; Gold et al. (1995) Ann. Rev. Biochem. 64:763–797; Tuerk and Gold (1990) Science 249:505–510). Aptamers have been selected to recognize a broad range of targets, including small organic molecules as well as large proteins (Gold et al. (1995) Ann. Rev. Biochem. 64:763–797; Osborne and Ellington (1997) Chem. Rev. 97:349–370). In most cases, affinities and specificities of aptamers to these targets are comparable or better than those of antibodies. In contrast to antibodies whose identification and production completely rest on animals and/or cultured cells, both the identification and production of aptamers takes place in vitro without any requirement for animals or cells. Aptamers are produced by solid phase chemical synthesis, an accurate and reproducible process with consistency among production batches. Aptamers are stable to long-term storage at room temperature. Moreover, once denatured, aptamers can easily be renatured, a feature not shared by antibodies. These inherent characteristics of aptamers make them attractive for diagnostic applications.

The SELEX process is a method for the in vitro evolution of nucleic acid molecules with highly specific binding to target molecules and is described in U.S. patent application Ser. No. 07/536,428, filed Jun. 11, 1990, entitled "Systematic Evolution of Ligands by Exponential Enrichment," now abandoned; U.S. patent application Ser. No. 07/714,131, filed Jun. 10, 1991, entitled "Nucleic Acid Ligands," now U.S. Pat. No. 5,475,096; U.S. patent application Ser. No. 07/931,473, filed Aug. 17, 1992, entitled "Methods for Identifying Nucleic Acid Ligands," now U.S. Pat. No. 5,270,163 (see also, WO 91/19813), each of which is specifically incorporated by reference herein in its entirety. Each of these applications, collectively referred to herein as the SELEX Patent Applications, describes a fundamentally novel method for making a nucleic acid ligand to any desired target molecule. The SELEX process provides a class of products which are referred to as nucleic acid ligands or aptamers, each ligand having a unique sequence, and which has the property of binding specifically to a desired target compound or molecule. Each SELEX process-identified nucleic acid ligand is a specific ligand of a given target compound or molecule. The SELEX process is based on the unique insight that nucleic acids have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," abandoned in favor of U.S. patent application Ser. No. 08/198,670, now U.S. Pat. No. 5,707,796, describes the use of the SELEX process in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands," now abandoned (see U.S. patent application Ser. No. 08/612,895, filed Mar. 8, 1996, entitled "Systematic Evolution of Ligands by Exponential Enrichment: Photoselection of Nucleic Acid Ligands and Solution SELEX, now U.S. Pat. No. 5,763,177), describes a SELEX process-based method for selecting nucleic acid ligands containing photoreactive groups capable of binding and/or photocrosslinking to and/or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443,957, now U.S. Pat. No. 5,580,737, describes a method for identifying highly specific nucleic acid ligands able to discriminate between closely related molecules, which can be non-peptidic, termed Counter-SELEX. U.S. patent application Ser. No. 08/143,564, filed Oct. 25, 1993, entitled "Systematic Evolution of Ligands by Exponential Enrichment: Solution SELEX," abandoned in favor of U.S. patent application Ser. No. 08/461,069, now U.S. Pat. No. 5,567,588, describes a SELEX process-based method which achieves highly efficient partitioning between oligonucleotides having high and low affinity for a target molecule.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. patent application Ser. No. 08/117,991, filed Sep. 8, 1993, entitled "High Affinity Nucleic Acid ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel 2' Modified Nucleosides by Intramolecular Nucleophilic Displacement," now abandoned, describes oligonucleotides containing various 2'-modified pyrimidines.

The SELEX method encompasses combining selected oligonucleotides with other selected oligonucleotides and non-oligonucleotide functional units as described in U.S.

patent application Ser. No. 08/284,063, filed Aug. 2, 1994, entitled "Systematic Evolution of Ligands by Exponential Enrichment: Chimeric SELEX," now U.S. Patent No. 5,637,459 and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties of oligonucleotides with the desirable properties of other molecules.

U.S. patent application Ser. No. 07/964,624, filed Oct. 21, 1992, entitled "Nucleic Acid Ligands to HIV-RT and HIV-1 Rev," now U.S. Pat. No. 5,496,938, describes methods for obtaining improved nucleic acid ligands after SELEX has been performed. U.S. patent application Ser. No. 08/400,440, filed Mar. 8, 1995, entitled "Systematic Evolution of Ligands by Exponential Enrichment: Chemi-SELEX," now U.S. Pat. No. 5,705,337, describes methods for covalently linking a ligand to its target.

The SELEX method further encompasses combining selected nucleic acid ligands with lipophilic compounds or non-immunogenic, high molecular weight compounds in a diagnostic or therapeutic complex as described in U.S. patent application Ser. No. 08/434,465, filed May 4, 1995, entitled "Nucleic Acid Ligand Complexes," now U.S. Pat. No. 6,011,020. VEGF nucleic acid ligands that are associated with a lipophilic compound, such as diacyl glycerol or dialkyl glycerol, in a diagnostic or therapeutic complex are described in U.S. patent application Ser. No. 08/739,109, filed Oct. 25, 1996, entitled "Vascular Endothelial Growth Factor (VEGF) Nucleic Acid Ligand Complexes," now U.S. Pat. No. 5,859,228. VEGF nucleic acid ligands that are associated with a lipophilic compound, such as a glycerol lipid, or a non-immunogenic, high molecular weight compound, such as polyethylene glycol, are further described in U.S. patent application Ser. No. 08/897,351, filed Jul. 21, 1997, entitled "Vascular Endothelial Growth Factor (VEGF) Nucleic Acid Ligand Complexes," now U.S. Pat. No. 6,051,698. VEGF nucleic acid ligands that are associated with a non-immunogenic, high molecular weight compound or lipophilic compound are also further described in PCT/US97/18944, filed Oct. 17, 1997, entitled "Vascular Endothelial Growth Factor (VEGF) Nucleic Acid Ligand Complexes." Each of the above described patent applications which describe modifications of the basic SELEX procedure are specifically incorporated by reference herein in their entirety.

It is an object of the present invention to provide methods that can be used to detect virtually any non-nucleic acid target molecule in a test mixture, using nucleic acid reagents that are easily and cheaply manufactured.

It is a further object of the instant invention to provide a method for adapting molecular beacons in order to detect non-nucleic acid target molecules in a test mixture.

Another object of the instant invention is to provide a single, universal assay for virtually any non-nucleic acid target molecule in which measurements of fluorescence emission are used to determine the concentration of the target.

SUMMARY OF THE INVENTION

The present invention includes methods for detecting the binding of nucleic acid ligands to their cognate target molecules. The methods rely on the insight that nucleic acid ligands can be recognized by molecular beacons in a target-dependent context. The methods and reagents described herein allow, for the first time, virtually the detection of virtually any target molecule.

The invention uses novel molecular beacons, termed ligand beacons, that hybridize to nucleic acid ligands only under preselected conditions. In some embodiments, the ligand beacon can only hybridize to nucleic acid ligands that are free of their cognate target; in other embodiments, the ligand beacon can only hybridize to nucleic acid ligands that are bound to their cognate targets. In either case, the binding of nucleic acid ligand to target is accompanied by a measurable change in the spectral properties of the ligand beacon. Conventional molecular beacons known in the art are used to recognize complementary nucleic acid sequences, e.g., genomic sequences and sequences specific to pathogens. By contrast, ligand beacons recognize nucleic acid ligands with both a particular sequence and a particular configuration. The configuration of the nucleic acid ligand changes when it is or is not bound to its cognate target.

In one embodiment the method for identifying the presence of a target molecule in a test mixture comprises: introducing a nucleic acid ligand to the target and a ligand beacon to the test mixture; wherein the ligand beacon comprises: a) a nucleic acid sequence complementary to at least a portion of the nucleic acid ligand, b) a fluorescent group, and c) a fluorescence-modifying group; wherein the emission profile of said fluorescent group is different when said target molecule is present in the test mixture from when said target molecule is not present; and measuring the fluorescence emission of said ligand beacon, whereby the presence of said target molecule is determined.

The methods described herein provide, for the first time, a single universal method for target molecule detection which simply involves analyzing fluorescence emission. The reagents and methods described herein are particularly suitable for diagnostic assays. Diagnostic assays that require quantitative measurements (e.g., measurements of a hormone or sugar level) are possible according to the present invention by simply comparing the fluorescence measurement with that obtained from a control. Similarly, diagnostic assays requiring qualitative detection of substances (e.g., the presence of a mutated gene product or the presence of a pathogen) are also possible. The reagents can be used in assays for single substances or they can be used to simultaneously monitor a variety of substances in a single assay. Using different fluorescent groups with spectroscopically resolvable emission spectra, this method allows for the simultaneous detection of multiple targets in a single vessel. In this homogeneous multiplexing approach, distinct fluorescent groups can be attached to different nucleic acid ligands specific to targets of interest.

In particular, the invention provides methods for performing assays using reagents attached to solid supports. In these embodiments, a plurality of nucleic acid ligands are attached to spatially discrete regions on solid supports, and contacted with the solution to be assayed. Using the detection methods described herein, measurements of fluorescence at discrete sites on the solid support can reveal whether particular substances are present in the assay solution and in what quantities. In this way, it is possible to assay for a plurality—potentially hundreds or even thousands—of different substances in a single test. Arrays of nucleic acid ligands that can be used with the methods and reagents described herein are detailed in U.S. patent application Ser. No. 08/990,436, filed Dec. 15, 1997, entitled "Nucleic Acid Ligand Diagnostic Biochip," now U.S. Pat. No. 6,242,246, which is incorporated herein by reference in its entirety.

The ligand beacon assay described here has several advantages. It is a homogeneous assay that can be performed in plasma. It is a general method to detect virtually any class of target molecule to which high affinity and specific nucleic acid ligand is available. It consists of three simple steps:— addition of a nucleic acid ligand/aptamer, addition of a ligand beacon and measurement of fluorescence. It is fast, requires less than 30 minutes, and amenable for high throughput screening. Since molecular beacons equipped with distinct fluorophores that emit at different wavelengths have been used to detect more than one target nucleic acid sequences in a single sample (Kostrikis et al. (1998) Science 279:1228–1229; Tyagi et al. (1998) Nature Biotechnology 16:49–53), the ligand beacon assay is also amenable for multiplexing. In some respects, this assay is quite analogous to fluorescence polarization competitive immunoassay that is currently used in the clinical routine (Wilson et al. (1998) Clin. Chem. 44:86–91).

The present invention also includes methods for the detection of target molecules in test mixtures through the use of a hybridization cascade involving a set of three or more mutually complementary oligonucleotides. In this method, a first nucleic acid binds to a target molecule and the nucleic acid undergoes a conformational change that exposes sequences to which other nucleic acids in the set can hybridize. The nucleic acids that hybridize to the first nucleic acid also undergo a conformational change during hybridization that similarly exposes sequences to which other nucleic acids in the set can hybridize. The sequences of the set of nucleic acids involved are chosen so that a cascade of hybridization can occur between the members of the set. This chain reaction of conformational change and hybridization will continue until one of the participating nucleic acids is depleted. Any nucleic acid structure that undergoes a hybridization-promoting conformational change upon (i) binding to a target molecule, and/or (ii) hybridizing to another nucleic acid, is contemplated in the subject methods.

In a preferred embodiment, a set of at least three single-stranded nucleic acids are used, wherein each nucleic acid has a domain with an intramolecular double helix. The sequences of the nucleic acids are chosen so that the regions that form the intramolecular helix in one member of the set will hybridize more stably to those regions of another member of the set than to one another. For example, the set could comprise sequences as follows wherein the letters A, B and C signify a unique sequence in the intramolecular helical region, "/" signifies imperfect intramolecular base pairing and "'" signifies a complementary sequence: (i) A/B, (ii) B'/C, (iii) C'/A'. Thus, if the first nucleic acid is A/B and these sequences become available for intermolecular base-pairing upon target molecule binding, then the A segment will then bind to the A' segment of C'/A', and the B segment will bind to the B' segment of B'/C. This in turn allows the C and C' portions of the newly bound nucleic acids to bind to their complementary sequences in C'/A' and B'/C respectively. These reactions occur because intermolecular helix formation is more energetically favored than intramolecular helix formation. This cascade of intermolecular helix formation between the three members of the set results in the formation of a multimolecular hybridization complex.

The cascade of hybridization described is triggered by the conformational change of the first nucleic acid upon binding to the target molecule. In the case of nucleic acids with an intramolecular double helix, this conformational change is the dissolution of the intramolecular helix of the first nucleic acid. This exposes the antiparallel strands that comprise the double helix, and allows them to participate in hybridization reactions. This disruption will occur when the target molecule binding region of the nucleic acid binds to a specific target molecule.

In some embodiments, the target-binding region of the first nucleic acid will hybridize through Watson-Crick interactions to a target nucleic acid with sequence complementary to at least part of the loop region. Hence, binding of a single molecule of the first nucleic acid to a single target nucleic acid will initiate the formation of the multimolecular complex described above.

In other embodiments, the target-binding region is a nucleic acid ligand comprised of sequences that can bind to a non-nucleic acid target molecules through non-Watson-Crick interactions. Binding to a target molecule will bring about the same cascade of intermolecular hybridizations as described above.

BRIEF DESCRIPTION OF THE DRAWINGS

FIGS. 2A–C illustrate schematically the principle behind the ligand beacon assay. FIG. 2A illustrates the interaction of an aptamer (nucleic acid ligand) with a molecular beacon (ligand beacon) whose nucleotide sequence in the loop is complementary to a nucleotide stretch in the aptamer. This interaction causes the spatial separation of the fluorophore (star) from the quencher (pentagon) producing a fluorescence signal. In FIG. 2B the aptamer-specific target protein binds to the aptamer in a specific and high affinity manner, thereby protecting the aptamer from interaction with the ligand beacon. When the aptamer-specific target is present in excess the addition of the ligand beacon would not generate fluorescence. FIG. 2C depicts the expected change in fluorescence signal as a function of the log of the concentration of the target. When the concentration of the target is exceedingly low, virtually all the aptamer molecules are available for generating high signal upon interacting with the ligand beacon (upper box). When the target is in great excess to that of the aptamer, there is virtually no free aptamer available to generate signal upon hybridization to the ligand beacon (lower box). When the target concentration is not at these two extremes, the fluorescence signal is inversely proportional to the concentration of the target (middle box).

FIG. 3B depicts the primary structures of the ligand beacons used in the study. These sequences are designed to fold into stem-loop structures in which five nucleotides (bold) in the termini form the stem, whereas the nucleotide stretch in the middle (italics) forms the loop. The 5' terminus of each ligand beacon carries the fluorophore, fluorescein (F), whereas the 3' terminus contains DABCYL as the quencher (Q).

FIG. 4A depicts the results of the interaction of the PDGF aptamer with its ligand beacon. Closed circles indicate the signal generated by the ligand beacon specific to the PDGF aptamer upon interaction with the PDGF aptamer with predicted 3-way junction structure. Open circles represent the signal generated by the same ligand beacon when incubated with the truncated sequence (indicated in bold in FIG. 3A) without the extra nucleotides in the aptamer. Stars indicate the signal generated by the same ligand beacon when mixed with the Taq aptamer.

FIG. 7A illustrates the detection of low concentrations of L-selectin with 200 nM each of L-selectin aptamer and L-selectin ligand beacon. FIG. 7B illustrates the detection of high concentrations of L-selectin with 800 nM each of L-selectin aptamer and L-selectin ligand beacon.

FIG. 9A illustrates the results of a ligand beacon assay for human PDGF AB-dimer in plasma, FIG. 9B illustrates the results of a ligand beacon assay for human L-selectin in plasma and FIG. 9C illustrates the results of a ligand beacon assay for human P-selectin in plasma.

FIGS. 14A–D illustrate an example of cascade hybridization using three different stem-loop sequences.

DETAILED DESCRIPTION OF THE INVENTION

Figure 1:
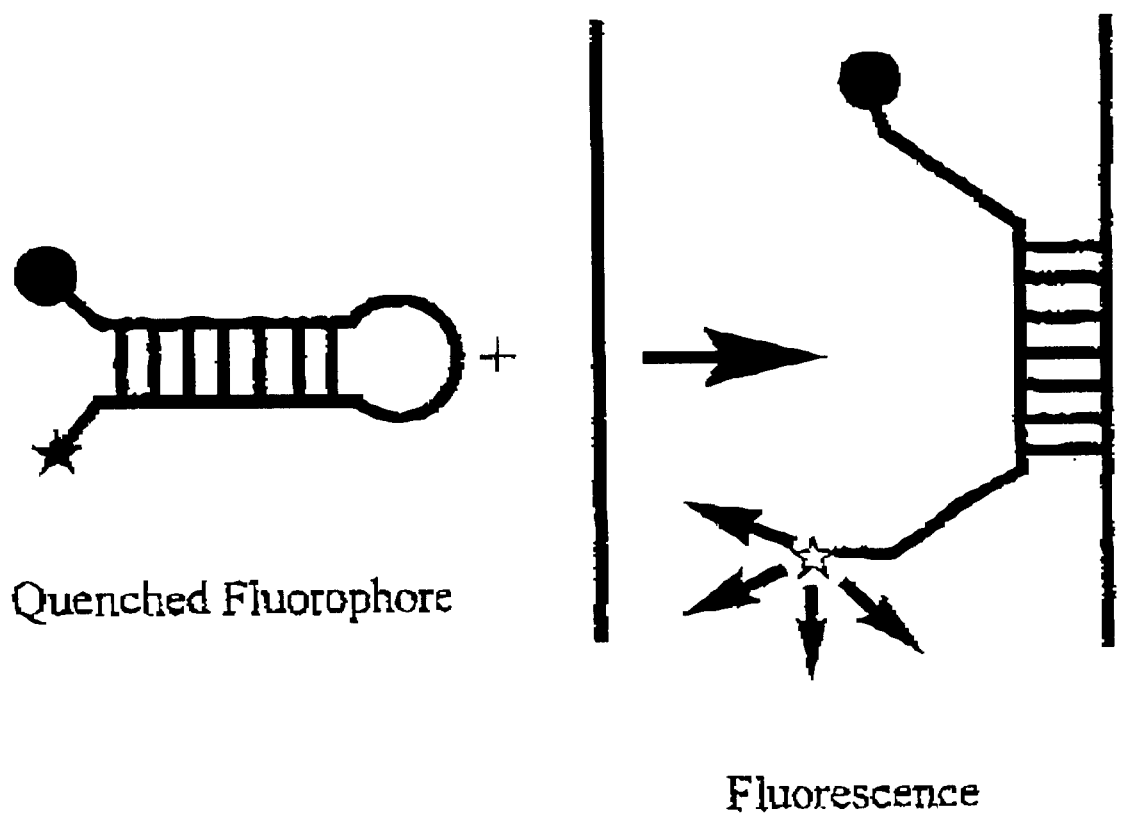
FIG. 1 depicts the use of molecular beacons, wherein the star represents a fluorescent group and the filled circle represents a quenching group. Separation of the quenching group from the fluorescent group upon binding of the nucleic acid leads to the production of a fluorescent signal.

The present invention describes methods for the detection and/or quantitation of virtually any target molecule in a mixture. The invention uses novel molecular beacons, termed ligand beacons, that hybridize to nucleic acid ligands only under preselected conditions. In some embodiments, the ligand beacon can only hybridize to nucleic acid ligands that are free of their cognate target; in other embodiments, the ligand beacon can only hybridize to nucleic acid ligands that are bound to their cognate targets. In either case, the binding of nucleic acid ligand to target is accompanied by a measurable change in the properties of the ligand beacon.

In one embodiment the method for identifying the presence of a target molecule in a test mixture comprises: introducing a nucleic acid ligand to the target and a ligand beacon to the test mixture; wherein the ligand beacon comprises: a) a nucleic acid sequence complementary to at least a portion of the nucleic acid ligand, b) a fluorescent group, and c) a fluorescence-modifying group; wherein the emission profile of said fluorescent group is different when said target molecule is present in the test mixture from when said target molecule is not present; and measuring the fluorescence emission of said ligand beacon, whereby the presence of said target molecule is determined. In this embodiment, the present invention provides a single universal method for target molecule detection which simply involves analyzing fluorescence emission.

The reagents and methods described herein are particularly suitable for diagnostic assays. Diagnostic assays that require quantitative measurements (e.g., measurements of a hormone or sugar level) are possible according to the present invention by simply comparing the fluorescence measurement with that obtained from a control. Similarly, diagnostic assays requiring qualitative detection of substances (e.g., the presence of a mutated gene product or the presence of a pathogen) are also possible. The reagents can be used in assays for single substances or they can be used to simultaneously monitor a variety of substances in a single assay. Using different fluorescent groups with spectroscopically resolvable emission spectra, this method allows for the simultaneous detection of multiple targets in a single vessel. In this homogeneous multiplexing approach, distinct fluorescent groups can be attached to different nucleic acid ligands specific to targets of interest.

In another embodiment, this invention provides methods for performing assays using reagents attached to solid supports. In this embodiment, a plurality of nucleic acid ligands are attached to spatially discrete regions on solid supports, and contacted with the solution to be assayed. Using the detection methods described herein, measurements of fluorescence at discrete sites on the solid support can reveal whether particular substances are present in the assay solution and in what quantities. In this way, it is possible to assay for a plurality—potentially hundreds or even thousands—of different substances in a single test. Arrays of nucleic acid ligands that can be used with the methods and reagents described herein are detailed in U.S. patent application Ser. No. 08/990,436, filed Dec. 15, 1997, entitled "Nucleic Acid Ligand Diagnostic Biochip," now U.S. Pat. No. 6,242,246, which is incorporated herein by reference in its entirety.

The ligand beacon assay described herein is a homogeneous assay that can be performed in plasma, it is a general method to detect virtually any class of target molecule to which high affinity and specific nucleic acid ligand is available, it consists of three simple steps:—addition of a nucleic acid ligand/aptamer, addition of a ligand beacon and measurement of fluorescence, it fast, requiring less than 30 minutes and is amenable for high throughput screening.

The present invention also includes methods for the detection of target molecules in test mixtures through the use of a hybridization cascade involving a set of three or more mutually complementary oligonucleotides. Cascade hybridization can be used to detect exceedingly low concentrations of the target molecule by virtue of a highly efficient signal amplification mechanism.

Various terms are used herein to refer to aspects of the present invention. To aid in the clarification of the description of the components of this invention, the following definitions are provided.

"Nucleic acid" means either DNA, RNA, single-stranded or double-stranded, and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases isocytidine and isoguanidine and the like. Modifications can also include 3' and 5' modifications such as capping.

"Nucleic acid ligand" refers to a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In a preferred embodiment, the action is specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids (the SELEX process).

Nucleic acid ligand includes nucleic acid sequences that are substantially homologous to the nucleic acid ligands actually isolated by the SELEX method. By substantially homologous it is meant a degree of primary sequence homology in excess of 70%, most preferably in excess of 80%. In the past it has been shown that various nucleic acid ligands to a specific target with little or no primary homology may have substantially the same ability to bind the target. For this reason, this invention also includes nucleic acid ligands that have substantially the same ability to bind a target as the nucleic acid ligands identified by the SELEX process. Substantially the same ability to bind a target means that the affinity is within a few orders of magnitude of the affinity of the ligands described herein. It is well within the skill of those of ordinary skill in the art to determine whether a given sequence—substantially homologous to those specifically described herein—has substantially the same ability to bind a target.

The term "aptamer" is used interchangeably with the term "nucleic acid ligand."

"Target" means any compound or molecule of interest for which a diagnostic test is desired and where a nucleic acid ligand is known or can be identified. A target can be a protein, peptide, nucleic acid, lipid, carbohydrate, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, etc. without limitation. A target can also be modified in certain ways to enhance the likelihood of an interaction between the target and the nucleic acid.

"Candidate mixture" refers to a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

The "SELEX™" methodology involves the combination of selection of nucleic acid ligands which interact with a target in a desirable manner, for example binding to a protein, with amplification of those selected nucleic acids. Optional iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. The SELEX methodology is described in the SELEX Pat. Applications.

"Cascade hybridization" as defined herein refers to a process whereby the binding of a nucleic acid to a target molecule promotes the formation of a multimolecular complex comprising several different mutually complementary nucleic acids associated with one another through Watson-Crick interactions.

"Energy transfer" refers to a process whereby an energy donating chemical group upon excitation with light of a particular wavelength yields a photon of a specific wavelength, whereupon said photon is captured and absorbed by an energy accepting group before said can be spectroscopically detected.

"Solid support" refers to any of a number of supports to which molecules may be attached through either covalent or non-covalent bonds. The solid supports can be beads, filters or microfabricated surfaces, such as biochips. Solid supports are typically made of inert materials that are functionalized on their surface to allow for the attachment of nucleic acids. This includes, but is not limited to, Langmuir-Bodgett films, functionalized glass, membranes, charged paper, nylon, germanium, silicon, PTFE, polystyrene, gallium arsenide, gold and silver. Any other material known in the art that is capable of having functional groups such as amino, carboxyl, thiol or hydroxyl, incorporated on its surface is contemplated. This includes surfaces with any topology, such spherical surfaces and grooved surfaces.

"Bodily fluid" refers to a mixture of molecules obtained from an organism. Bodily fluids include, but are not limited to, whole blood, blood plasma, urine, semen, saliva, lymph fluid, meningal fluid, amniotic fluid, glandular fluid, sputum and cerebrospinal fluid. Bodily fluid also includes experimentally separated fractions of all of the preceding and solutions or mixtures containing homogenized solid material, such as feces, tissues and biopsy samples.

"Test mixture" refers to any sample that contains a plurality of molecules. This includes, but is not limited to, bodily fluids as defined above, and any sample for environmental and toxicology testing such as contaminated water and industrial effluent.

"Fluorescent group" refers to a molecule that, when excited with light having a selected wavelength, emits light of a different wavelength. Fluorescent groups include, but are not limited to, fluorescein, tetramethylrhodamine, Texas Red, BODIPY, 5-[(2-aminoethyl)amino]napthalene-1-sulfonic acid (EDANS), coumarin and Lucifer yellow. Fluorescent groups may also be referred to as "fluorophores".

"Fluorescence-modifying group" refers to a molecule that can alter in any way the fluorescence emission from a fluorescent group. A fluorescence-modifying group generally accomplishes this through an energy transfer mechanism. Depending on the identity of the fluorescence-modifying group, the fluorescence emission can undergo a number of alterations, including, but not limited to, attenuation, complete quenching, enhancement, a shift in wavelength, a shift in polarity, a change in fluorescence lifetime. One example of a fluorescence-modifying group is a quenching group.

"Energy transfer" refers to the process by which the fluorescence emission of a fluorescent group is altered by a fluorescence-modifying group. If the fluorescence-modifying group is a quenching group, then the fluorescence emission from the fluorescent group is attenuated (quenched). Energy transfer can occur through fluorescence resonance energy transfer or through direct energy transfer. The exact energy transfer mechanisms in these two cases are different. It is to be understood that any reference to energy transfer in the instant application encompasses all of these mechanistically-distinct phenomena.

"Energy transfer pair" is used to refer to a group of molecules that form a single complex within which energy transfer occurs. Such complexes may comprise, for example, two fluorescent groups which may be different from one another and one quenching group, two quenching groups and one fluorescent group, or multiple fluorescent groups and multiple quenching groups. In cases where there are multiple fluorescent groups and/or multiple quenching groups, the individual groups may be different from one another e.g., one complex contemplated herein comprises fluorescein and EDANS as fluorescent groups, and DABCYL as a quenching agent.

"Quenching group" refers to any fluorescence-modifying group that can attenuate at least partly the light emitted by a fluorescent group. We refer herein to this attenuation as "quenching." Hence, illumination of the fluorescent group in the presence of the quenching group leads to an emission signal that is less intense than expected, or even completely absent. Quenching occurs through energy transfer between the fluorescent group and the quenching group. The preferred quenching group of the invention is (4-dimethylamino-phenylazo)benzoic acid (DABCYL).

"Fluorescence resonance energy transfer" or "FRET" refers to an energy transfer phenomenon in which the light emitted by the excited fluorescent group is absorbed at least partially by a fluorescence-modifying group. If the fluorescence-modifying group is a quenching group, then that group can either radiate the absorbed light as light of a different wavelength or it can dissipate it as heat. FRET depends on an overlap between the emission spectrum of the fluorescent group and the absorption spectrum of the quenching group. FRET also depends on the distance between the quenching group and the fluorescent group. Above a certain critical distance, the quenching group is unable to absorb the light emitted by the fluorescent group or can do so only poorly.

"Direct energy transfer" refers to an energy transfer mechanism in which passage of a photon between the fluorescent group and the fluorescence-modifying group does not occur. Without being bound by a single mechanism, it is believed that in direct energy transfer, the fluorescent group and the fluorescence-modifying group interfere with each others electronic structure. If the fluorescence-modifying group is a quenching group, this will result in the quenching group preventing the fluorescent group from even emitting light. Quenching groups and fluorescent groups are frequently close enough together in the stem of ligand beacons that direct energy transfer can take place. For example, when DABCYL is located on one terminus of a ligand beacon, this quenching group can efficiently quench almost all fluorescent groups on the other terminus through direct energy transfer.

In general, quenching by direct energy transfer is more efficient than quenching by FRET. Indeed, some quenching groups that do not quench particular fluorescent groups by FRET (because they do not have the necessary spectral overlap with the fluorescent group) can do so efficiently by direct energy transfer. Furthermore, some fluorescent groups can act as quenching groups themselves if they are close enough to other fluorescent groups to cause direct energy transfer. For example, under these conditions, two adjacent fluorescein groups can quench one another's fluorescence effectively. For these reasons, there is no limitation on the nature of the fluorescent groups and quenching groups useful for the practice of this invention.

"Ligand beacon" refers to a nucleic acid molecule, labeled with an energy transfer pair, that can specifically hybridize to a nucleic acid ligand under preselected conditions. Upon doing so, the ligand beacon undergoes a conformational change that causes the members of the energy transfer pair to move relative to one another such that the emission from the fluorescent group is modified. Preferred energy transfer pairs comprise a fluorescent group and a quenching group. In preferred embodiments, the ligand beacon comprises a unimolecular stem-loop nucleic acid, wherein the fluorescent group and the quenching group are at the termini of the nucleic acid, and the loop comprises sequences that are at least partially complementary to sequences within the nucleic acid ligand. In some embodiments, the ligand beacon can only hybridize to the nucleic acid ligand when the nucleic acid ligand is not bound to its target. In other embodiments, the ligand beacon can only hybridize when the nucleic acid ligand is bound to its cognate target. In either case, hybridization of the ligand beacon to the nucleic acid ligand is accompanied by a change in the fluorescence emission intensity of the ligand beacon.

Although the ligand beacon comprises a unimolecular stem-loop nucleic acid in preferred embodiments, there is no limitation on the structure of the ligand beacon. Any nucleic acid that can hybridize to a nucleic acid ligand, and in doing so undergo a conformational change that alters the distance between nucleotides, is contemplated in the instant invention. For example, nucleic acids configured as G-quartets may be useful in this invention. These nucleic acid structures are formed by hydrogen bonding between the Hoogsteen and Watson-Crick faces of four spatially adjacent guanosines. Adjacent quartets can stack on top of one another to form a highly symmetric and regular complex. Similarly, ligand beacons that undergo conformational changes in which initially separated nucleotide positions become adjacent upon hybridizing to nucleic acid ligands are also included in the invention. These latter ligand beacons, when labeled with fluorescent groups and quenching groups at the appropriate nucleotide positions, undergo a decrease in fluorescence intensity upon binding to the nucleic acid ligand.

In a preferred embodiment, the nucleic acid ligands of the present invention are derived using the SELEX process, which is described in U.S. patent application Ser. No. 07/536,428, filed Jun. 11, 1990, entitled "Systematic Evolution of Ligands by EXponential Enrichment," now abandoned, U.S. patent application Ser. No. 07/714,131, filed Jun. 10, 1991, entitled "Nucleic Acid Ligands," now U.S. Pat. No. 5,475,096 and U.S. patent application Ser. No. 07/931,473, filed Aug. 17, 1992, entitled "Methods for Identifying Nucleic Acid Ligands," now U.S. Pat. No. 5,270,163 (see also, WO 91/19813). These applications, each specifically incorporated herein by reference, are collectively called the SELEX Patent Applications.

The SELEX process provides a class of products which are nucleic acid molecules, each having a unique sequence, and each of which has the property of binding specifically to a desired target compound or molecule. Target molecules are preferably proteins, but can also include among others carbohydrates, peptidoglycans and a variety of small molecules. SELEX methodology can also be used to target biological structures, such as cell surfaces or viruses, through specific interaction with a molecule that is an integral part of that biological structure.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity for the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX process provides high affinity ligands to a target molecule. This represents a singular achievement that is unprecedented in the field of nucleic acids research.

Certain chemical modifications of the nucleic acid ligand which can be made to increase the in vivo stability of the nucleic acid ligand or to enhance or to mediate the delivery of the nucleic acid ligand. See, e.g., U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, now U.S. Pat. No. 5,660,985, that describes oligonucleotides containing nucleotide derivatives chemically modified at the 5- and 2'-positions of pyrimidines. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

The modifications can be pre- or post-SELEX process modifications. Pre-SELEX process modifications yield nucleic acid ligands with both specificity for their SELEX target and improved in vivo stability. Post-SELEX process modifications made to 2'-OH nucleic acid ligands can result in improved in vivo stability without adversely affecting the binding capacity of the nucleic acid ligand.

Other modifications are known to one of ordinary skill in the art. Such modifications may be made post-SELEX process (modification of previously identified unmodified ligands) or by incorporation into the SELEX process.

Ligand Beacons—Assay Design

In one embodiment of the invention, a ligand beacon is used to detect a nucleic acid ligand that is or is not bound to its cognate target. The ligand beacon preferably consists of a single-stranded DNA molecule that assumes a stem-loop structure in solution (FIG. 2A). In this embodiment, the stem of the ligand beacon is formed by the intramolecular base-pairing of two antiparallel strands of the nucleic acid. The 5' terminus of one strand is linked to the 3' terminus of the other strand with a loop of single stranded DNA. These nucleic acid molecules can be rapidly synthesized as single-stranded oligonucleotides with the general structure:

wherein sequence A' is both complementary in sequence and reversed in orientation relative to A. When heat-denatured and slowly cooled, this oligonucleotide will form a stem-loop structure wherein the dashed line forms the loop, and wherein A and A' pair to form the stem. The loop domain comprises sequences that are at least partially complementary to a region of the nucleic acid ligand. In preferred embodiments, the sequences are chosen such that they can only hybridize to one another when the nucleic acid ligand is not bound to its cognate target. Furthermore, when the ligand beacon hybridizes to the nucleic acid ligand, the nucleic acid ligand can no longer bind to its cognate target. In particularly preferred embodiments, the loop of the ligand beacon binds to a sequence in the nucleic acid ligand that is at least about 20 nucleotides long; the stem region of the ligand beacon is preferably shorter.

The formation of the intermolecular duplex between the loop of the ligand beacon and the target-free nucleic acid ligand is energetically favored because the resulting duplex is longer, and hence more stable, than the intramolecular duplex. As the loop sequence and the nucleic acid ligand form a duplex, torsional forces are developed in the ligand beacon. These forces are transmitted to the stem region which unwinds in response, usually starting at the base of the stem where the termini are located. One base pair in the stem is unwound for each new base pair that is made between the ligand beacon and the nucleic acid ligand. Thus, nucleotide positions that were adjacent to one another on opposite sides of the stem become separated. In particular, because unwinding begins at the base of the stem, the termini of the ligand beacon become widely separated.

In some embodiments, nucleotide positions in the ligand beacon that become separated from one another are labeled with an energy transfer pair. The preferred energy transfer pair of the instant invention comprises a quenching group and a fluorescent group. In preferred embodiments, the nucleotide positions on the ligand beacon that are labeled with the quenching group and the fluorescent group are chosen from those that form the intramolecular stem. In especially preferred embodiments, the 5' and 3' termini of the ligand beacon are labeled with these groups, as the termini become widely separated upon hybridization to the nucleic acid ligand.

The fluorescent group and the adjacent quenching group take part in energy transfer. In some instances, the energy transfer occurs through fluorescence resonance energy transfer (FRET). FRET takes place when fluorescence emission from a fluorescent group is transferred to an adjacent group that somehow modifies the signal (in this case, quenching the signal). This effect is strongly dependent on the distance between the two groups, such that when separated by a critical distance, FRET does not take place, and the fluorescence emission is unmodified. FRET also requires that the emission spectrum of the fluorescent group overlaps with the absorbance spectrum of the modifying group.

Figure 2C:
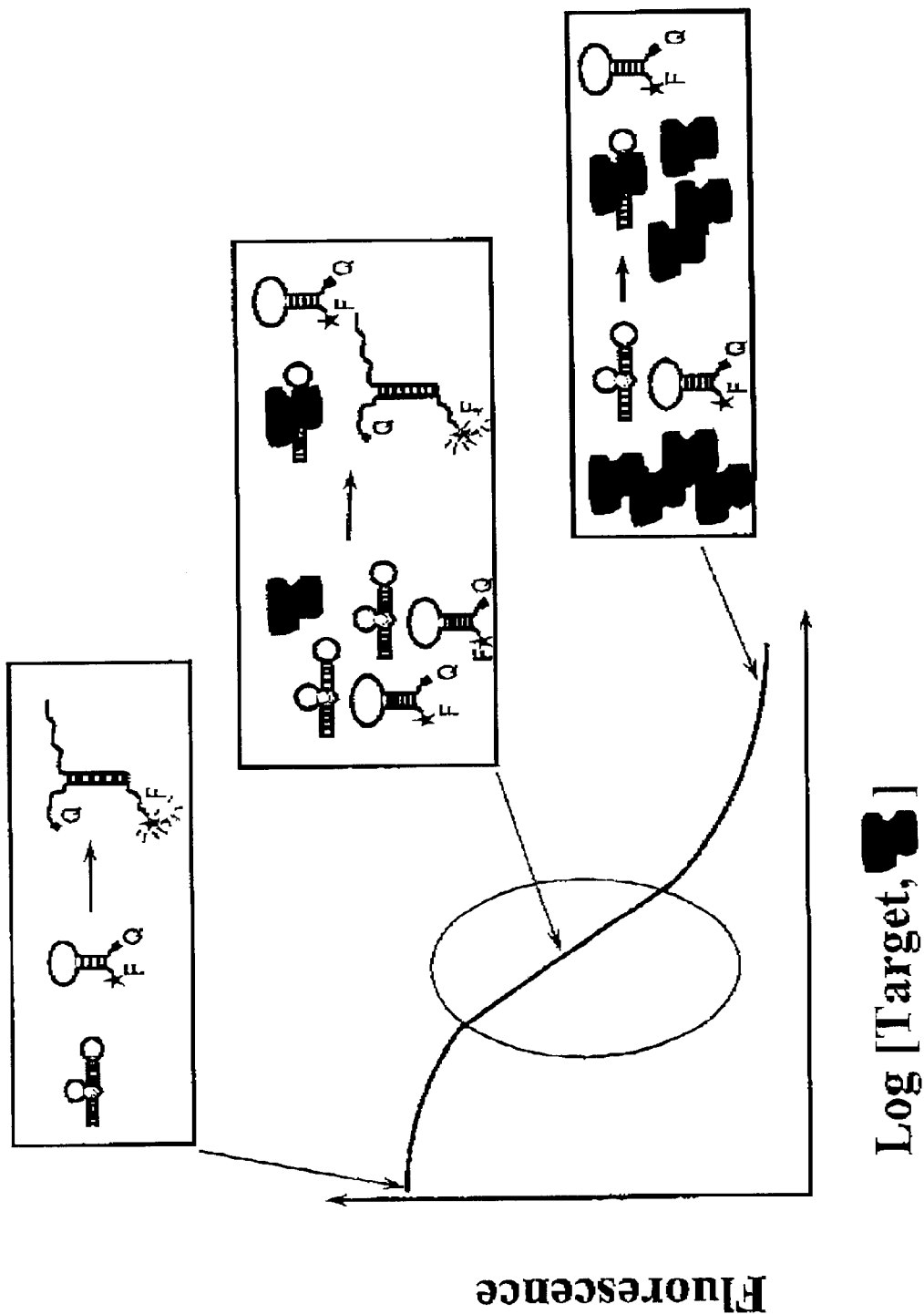
Figures 1, 3A:
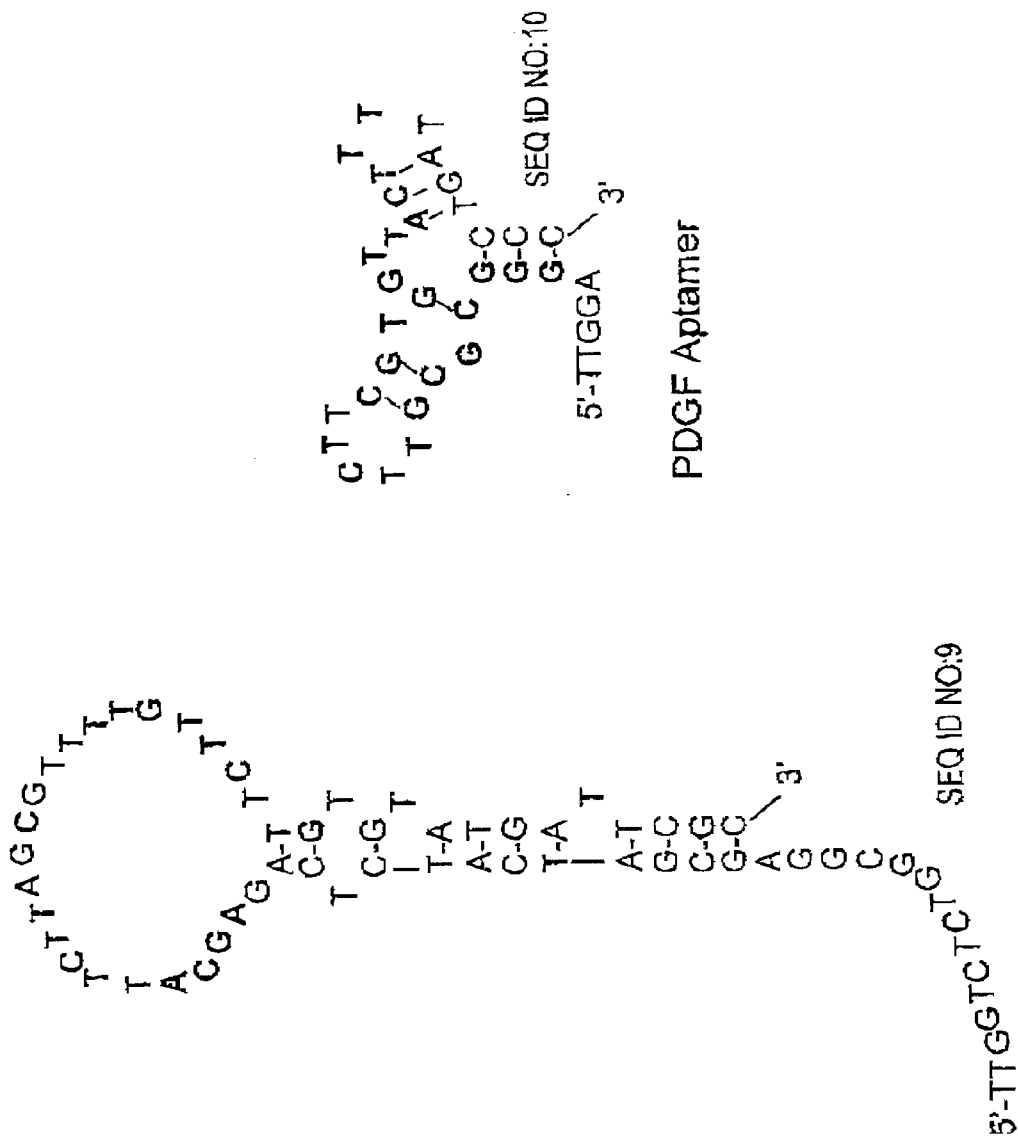
FIG. 3A depicts the primary and predicted secondary structures of Taq aptamer (SEQ ID NO:9), PDGF aptamer (SEQ ID NO:10), L-selectin aptamer (SEQ ID NO:11) and P-selectin aptamer (SEQ ID NO:12). P-selectin aptamer is an RNA-based aptamer in which all pyrimidine nucleotides have 2'-F substitutions on the sugar. All other aptamers are DNA-based sequences. Nucleotide stretches indicated in bold are complementary to the loop sequences in cognate ligand beacons shown in FIG. 3B.
Figures 2, 3A:
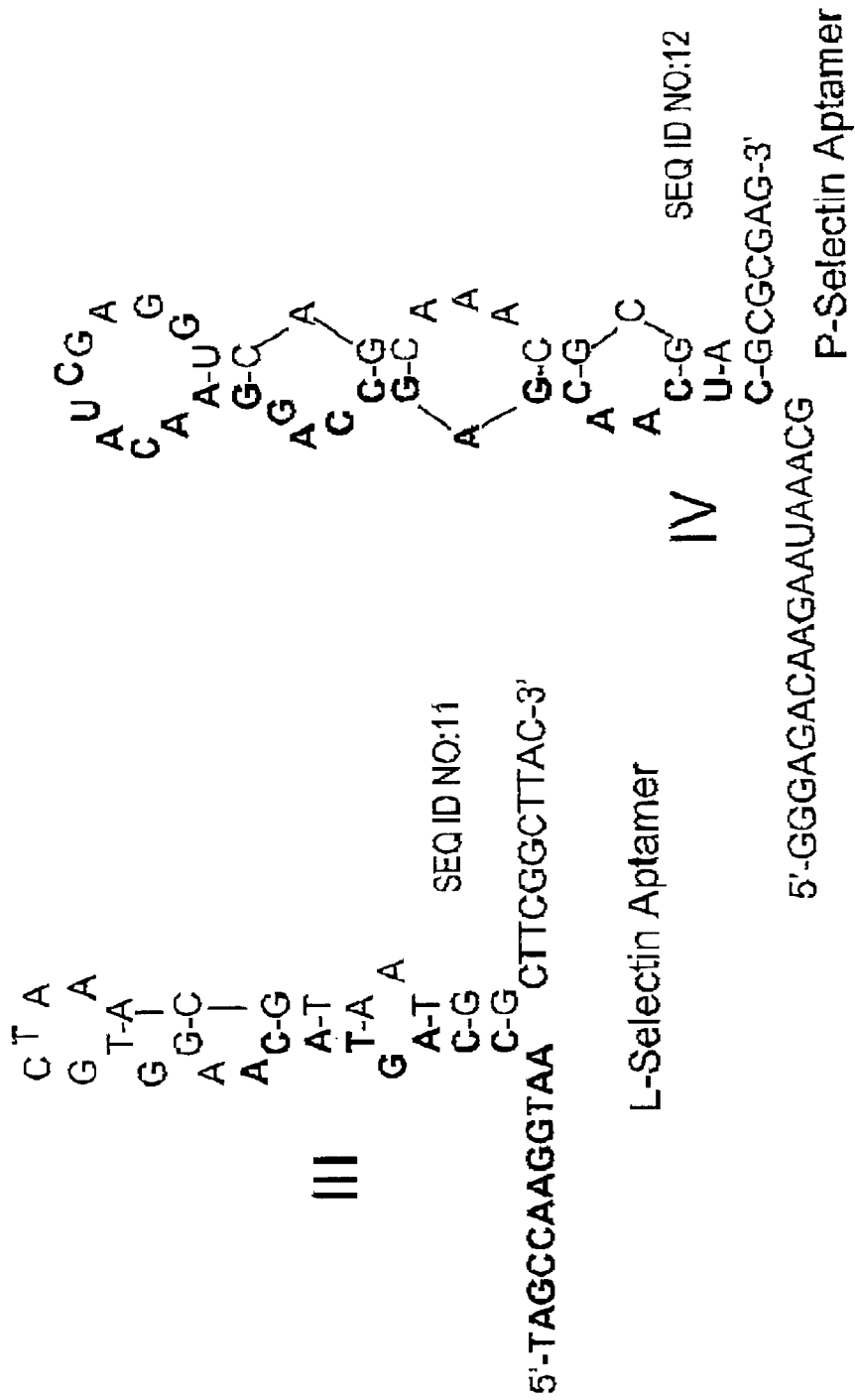

The principle behind an assay that employs a molecular beacon and a nucleic acid ligand based aptamer to detect molecular targets is schematically illustrated in FIGS. 2A–2C. With reference to FIG. 2, a nucleic acid-based aptamer acts as a sensor that detects the presence of a specific target molecule, for example, a protein, and in turn, communicates with the molecular beacon. Here, the nucleotide sequence in the loop of the molecular beacon is complementary to a nucleotide stretch within an aptamer such that the hybridization of the two species will lead to the generation of a fluorescence signal (FIG. 2A). When the aptamer-specific molecular target is present in excess, the aptamer binds to it with high affinity, making the aptamer unavailable for subsequent hybridization with the molecular beacon (FIG. 2B). As a result, the molecular beacon remains dark when the concentration of the aptamer-specific target exceeds the concentration of the aptamer. When the target concentration is limiting, the amount of free aptamer available for hybridization with the molecular beacon is inversely proportional to the amount of the target present (FIG. 2C). Hence, the amount of fluorescence signal generated by a fixed amount of molecular beacon and a fixed amount of aptamer is inversely proportional to the concentration of the target.

The detection range of the assay is set by the concentration of the aptamer/ligand beacon pair. Higher concentrations of proteins are detected by increasing the concentration of these two species. The lower limit of detection of the assay is dictated by the inherent sensitivity of the reporter, the fluorophore, attached to the ligand beacon.

In the instant invention, the preferred fluorescent groups are fluorescein, tetramethylrhodamine and 5-[(2-aminoethyl)amino]napthalene-1-sulfonic acid (EDANS). The preferred quencher is (4-dimethylaminophenylazo) benozoic acid (DABCYL). When DABCYL and fluorescein or EDANS are close enough together for FRET to occur, DABCYL absorbs light emitted from the fluorescein or EDANS, and dissipates the absorbed energy as heat. As mentioned above, this effect is strongly dependent on the distance between the group. For example, at separations greater than 60 Å, DABCYL is unable to quench the fluorescence from EDANS. DABCYL itself is non-fluorescent at the wavelengths used to excite EDANS or fluorescein.

In other embodiments, the fluorescent group and the quenching group take place in a form of energy transfer termed direct energy transfer. Direct energy transfer occurs when the fluorescent group and the quenching group directly perturb each others electronic structure. When a direct transfer takes place, it is possible for a quenching group to quench at a much higher efficiency and over a broader spectrum than in FRET. Indeed, it has been reported that paired-groups that do not even display FRET, such as Texas Red and DABCYL, can be made to undergo direct energy transfer, leading to the efficient quenching of the fluorescence group by the other group. For example, it has been reported that under such circumstances, the quenching group DABCYL can quench almost all fluorophores (with emission spectra ranging from 475 nm–615 nm) with close to 100% efficiency (Tyagi et al. (1998) Nature Biotechnology 16:49–53).

In one preferred embodiment, fluorescein and DABCYL function as a direct energy transfer pair when present at the 5' and 3' termini, even though they are not an efficient FRET pair. In other embodiments, nucleotide positions that form an individual base pair in the stem are labeled with the fluorescent group and the quenching group. Labeling at these positions also allows direct energy transfer to take place. It is even possible to get fluorescence quenching when two identical fluorescent groups, such as two fluorescein groups, are sufficiently close together.

There is no limitation in the present invention as to the nature of the energy transfer pair, and there is no limitation as to the exact mechanism by which they function together. All that is required is that the spectral properties of the energy transfer pair change in some measurable way as the distance between the individual members of the energy transfer pair is varied.

It is possible to label the ligand beacon with more than one of each member of an energy transfer pair. For example, in some embodiments, two or more nucleotides are labeled with fluorescent groups and the same number of nucleotides are labeled with quenching groups. In preferred embodiments, all of the fluorescent groups are attached to the nucleotides that comprise one strand of the stem, and all of the quenching groups are attached to the nucleotides that comprises the other strand. In these embodiments, more than one base pair in the stem is labeled with both a fluorescent group and a quenching group. Such ligand beacons may give an increased signal relative to singly-labeled ligand beacons upon unwinding of the stem.

Where more than one fluorescent group or more than one quenching group is used, it is not required that there be an equal number of the two groups. For example, the ligand beacon can be labeled with one fluorescent group and two quenching groups. If the sites of labeling are sufficiently close to one another, then more efficient quenching of the fluorescent group would be expected to result. Alternatively, if a given quenching group is capable of quenching more than one fluorescent group, then the separation of a single effective quenching group from multiple fluorescent groups would be expected to give an increased signal relative to separation from a single fluorescent group.

Labeling the ligand beacons with energy transfer pairs can be accomplished easily by standard methods well known in the art. For example, it is possible to incorporate the fluorescent group fluorescein into the ligand beacon at the 5' end during automated oligonucleotide synthesis of the sequence. The quenching group DABCYL can be attached to the ligand beacon by first incorporating an amino group at the 3' end during oligonucleotide synthesis, and then reacting the amino group after synthesis with the succinimidyl ester of DABCYL in anhydrous N,N-dimethyl formamide. Alternatively, DABCYL can be incorporated directly into the ligand beacon during oligonucleotide synthesis. It is important to note that these methods can be adapted to place the members of the energy transfer pair at any location desired in the ligand beacon. In some embodiments it may not be useful to have the labels at the termini. In some instances, for example, it may be preferable to label the stem of the ligand beacon at positions other than the 5' and 3' termini. This is because under certain conditions, the termini of the ligand beacon may temporarily unwind in the absence of free nucleic acid ligand; which can lead to background fluorescence.

It is possible to use fluorescent groups with molecules other than quenching groups. For example, a fluorescent group can be placed next to a modifying group that shifts the emission wavelength, polarizes the emission or even enhances it. All of these effects result from FRET.

Using the instant methods, it is possible to simultaneously detect multiple target molecules in a test solution using ligand beacons. In this method, each target molecule is recognized by a distinct nucleic acid ligand and each nucleic acid ligand can hybridize to a different ligand beacon. Each ligand beacon in the assay has at least a different loop sequence, specific for a particular nucleic acid ligand. However, it is not necessary that each ligand beacon has a different stem sequence, as the stem sequence does not impart the specificity of the ligand beacon, so it is possible to use a common stem for every ligand beacon. In addition, each ligand beacon is labeled with at least a different fluorescent group. For example, to detect two different targets, two different nucleic acid ligands and two different ligand beacons are required. For example, one ligand beacon may be labeled with fluorescein and DABCYL, and the second labeled with rhodamine and DABCYL. Therefore, the concentration of the two targets can be determined in the test solution by monitoring the increase in both fluorescein and rhodamine emission.

It is important to note that it is not necessary to have any structural information about a nucleic acid ligand when designing its cognate ligand beacon. Given the rapidity with which one can synthesize the ligand beacons, only simple, routine experimentation is required to design several different ligand beacons for each nucleic acid ligand, each ligand beacon recognizing a sequence that it at least partially unique. The candidate ligand beacons can be quickly tested to determine which one has the desired activity.

As described above, preferred embodiments use ligand beacons that can bind to nucleic acid ligands only when the nucleic acid ligand is not bound to its target. However, the invention also includes ligand beacons that function in the converse manner. Specifically, the invention also includes ligand beacons that can only hybridize to nucleic acid ligands that are bound to their cognate targets. For example, it is possible to obtain nucleic acid ligands that adopt a primary conformation in the absence of target, but undergo a conformational change upon target binding. Such a conformational change may cause regions of the nucleic acid ligand that are initially double-stranded to become single-stranded. The ligand beacon can hybridize to these single-stranded regions, but not when they are double-stranded. As a result, the increase in fluorescence intensity that occurs upon mixing the nucleic acid ligand, the ligand beacon and the target is directly proportional to the amount of the target.

In other embodiments, the ligand beacon has a structure in which nucleotide positions that are initially separated become adjacent upon hybridizing to the nucleic acid ligand. If these nucleotide positions are labeled as described above with a fluorescent group and a quenching group, then hybridization to the nucleic acid ligand results in a decrease in the ligand beacon's fluorescence emission.

Although the preferred ligand beacons of the invention have a stem-loop architecture, there is no limitation on the structure of ligand beacons. Any nucleic acid structure that undergoes a change in configuration upon hybridizing to a nucleic acid ligand wherein individual nucleotides move relative to one another in a reproducible manner is contemplated herein. It is possible to stack more than one G-quartet on top of each other under appropriate ionic conditions. In this embodiment of the invention, the nucleotides that are located between the G-quartet residues comprise the nucleic acid sequences complementary to the nucleic acid ligand. The G-quartet residues are labeled with the energy transfer pair(s); upon hybridization of the ligand beacon to the nucleic acid ligand, the G-quartet is disrupted, and the energy transfer pair(s) are separated.

In order to determine the concentration of a target molecule in a test mixture, it is preferable to first obtain reference data in which constant amounts of ligand beacon and nucleic acid ligand are contacted with varying amounts of target. The fluorescence emission of each of the reference mixtures is used to derive a graph or table in which target concentration is compared to fluorescence emission. For example, a ligand beacon that a) hybridizes to a target-free nucleic acid ligand; and b) has a stem-loop architecture with the 5' and 3' termini being the sites of fluorescent group and quenching group labeling, could be used to obtain such reference data. Such a ligand beacon would give a characteristic emission profile in which the fluorescence emission decreases as the target concentration increases in the presence of a constant amount of ligand beacon and nucleic acid ligand. Then, a test mixture with an unknown amount of target would be contacted with the same amount of first nucleic acid ligand and second ligand beacon, and the fluorescence emission would be determined. The value of the fluorescence emission would then be compared with the reference data to obtain the concentration of the target in the test mixture.

In some embodiments, the nucleic acid ligand becomes covalently attached to its target molecule in the assay. Methods for obtaining nucleic acid ligands with this capability are described in U.S. patent application Ser. No. 08/123,935, filed Sep. 17, 1993, entitled "Photoselection of Nucleic Acid Ligands," now abandoned (see U.S. patent application Ser. No. 08/612,895, filed Mar. 8, 1996, entitled "Systematic Evolution of Ligands by Exponential Enrichment: Photoselection of Nucleic Acid Ligands and Solution SELEX, now U.S. Pat. No. 5,763,177), which are specifically incorporated herein in their entirety.

The assays that are possible using ligand beacons are far simpler than conventional techniques for detecting non-nucleic acid target molecules. The assays require only three manipulations: a) addition of the nucleic acid ligand(s); b) addition of the ligand beacons; and c) measurement of the fluorescence. In many embodiments, there is no need to perform any washing steps to remove background signal, unlike the ELISA assays known in the art. Therefore, the present invention provides a single common method that can be applied to virtually any target molecule. Because of the simplicity of the assay, it is particularly well suited to high-throughout automated analysis for medical diagnostic purposes.

In some embodiments, the ligand beacons are used in assays in which nucleic acid ligands are attached to the surface of a solid support. Methods for attaching nucleic acids to solid supports are well known in the art. In these assays, the fluorescence emission from the solid support is monitored after the solid support is contacted with the test mixture suspected of containing the target, and the ligand beacon. It is also possible to use multiple ligand beacons in assays in which a plurality of different nucleic acid ligands are attached to spatially discrete addresses on a solid support forming an array. Nucleic acid ligand arrays are described in U.S. patent application Ser. No. 08/990,436, filed Dec. 15, 1997, entitled "Nucleic Acid Ligand Diagnostic Biochip," now U.S. Pat. No. 6,242,246, which is specifically incorporated herein by reference in its entirety. These assays require that each nucleic acid ligand is recognized by a different ligand beacon with at least a unique loop sequence and a unique fluorescent group, as described above. Measuring the fluorescence emission profile of each address on the array reveals the concentration of each target molecule.

In still further embodiments, one or more ligand beacons are attached to the solid support. Each ligand beacon can be attached via one of its termini by a spacer molecule to allow the ligand beacon to adopt the appropriate conformations without hindrance from the underlying solid support. A test mixture is contacted with one or more nucleic acid ligands and the mixture is contacted with the solid support. Again, measurement of the fluorescent emission profile at each address of the array reveals the concentration of each target molecule in the test mixture.

The present invention also provides kits for the detection of particular targets in test mixtures. The kit comprises separate containers containing solutions of a nucleic acid ligand to the particular target, and containing solutions of the appropriate ligand beacon. In some embodiments, the kit comprises a solid support to which is attached the nucleic acid ligand to the particular target. In further embodiments, the kit further comprises a container containing a standardized solution of the target. With this solution, it is possible for the user of the kit to prepare a graph or table of fluorescence units vs. target concentration; this table or graph is then used to determine the concentration of the target in the test mixture.

Cascade Hybridization

In one embodiment of the instant invention, a set of at least three single-stranded nucleic acids is synthesized, each comprising sequences that can form a stem-loop motif. The sequences of the antiparallel arms that form the stem are chosen according to the following criteria: (i) each arm is only partially complementary to the opposing arm on the same molecule with which it forms an intramolecular double helix (the stem); and (ii) each arm is perfectly complementary to one of the arms of at least one other stem-loop nucleic acid. Any sequences with the ability to form imperfect intramolecular base-pairs and perfect intermolecular base-pairs are contemplated. The sequences are represented schematically in FIG. 10 as A, B and C and their respective complements A', B'and C'.

Figure 10:
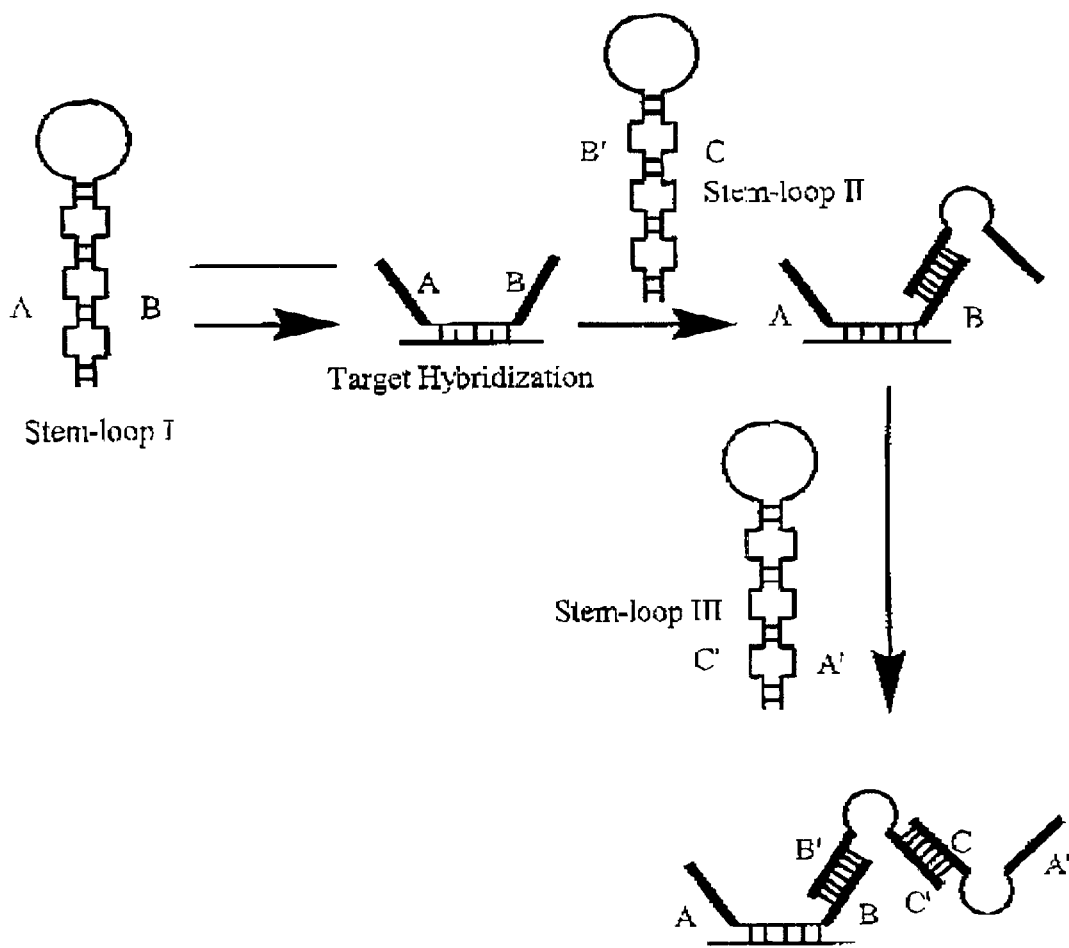
FIG. 10 depicts the early stages of a hybridization cascade using a stem-loop nucleic acid set.

FIG. 10 shows that A pairs imperfectly with B, B' pairs imperfectly with C and C' pairs imperfectly with A'. The loop region of each nucleic acid is represented as a curve. In one embodiment, the loop of stem-loop I comprises probe sequences that are complementary to a target nucleic acid that one would like to detect. Upon hybridization of the probe sequence to its cognate target, the arms AB will become unpaired. This will occur because the base pair formation between the loop and the target sequence is energetically more favored than that between the arms of the stem, and the structure adopted by the loop in order to bind to the target is not compatible with the stem structure. The sequences A and B of stem-loop I in FIG. 10 will now be available to hybridize with their complementary sequences. In FIG. 10, B can pair with the sequences B' from stem-loop II, which in turn makes the sequence C available for hybridization with the C' sequence from stem-loop III. In each case, the formation of the perfect intermolecular double helices is energetically favored once the base pairs between A and B are disrupted.

Figure 11:
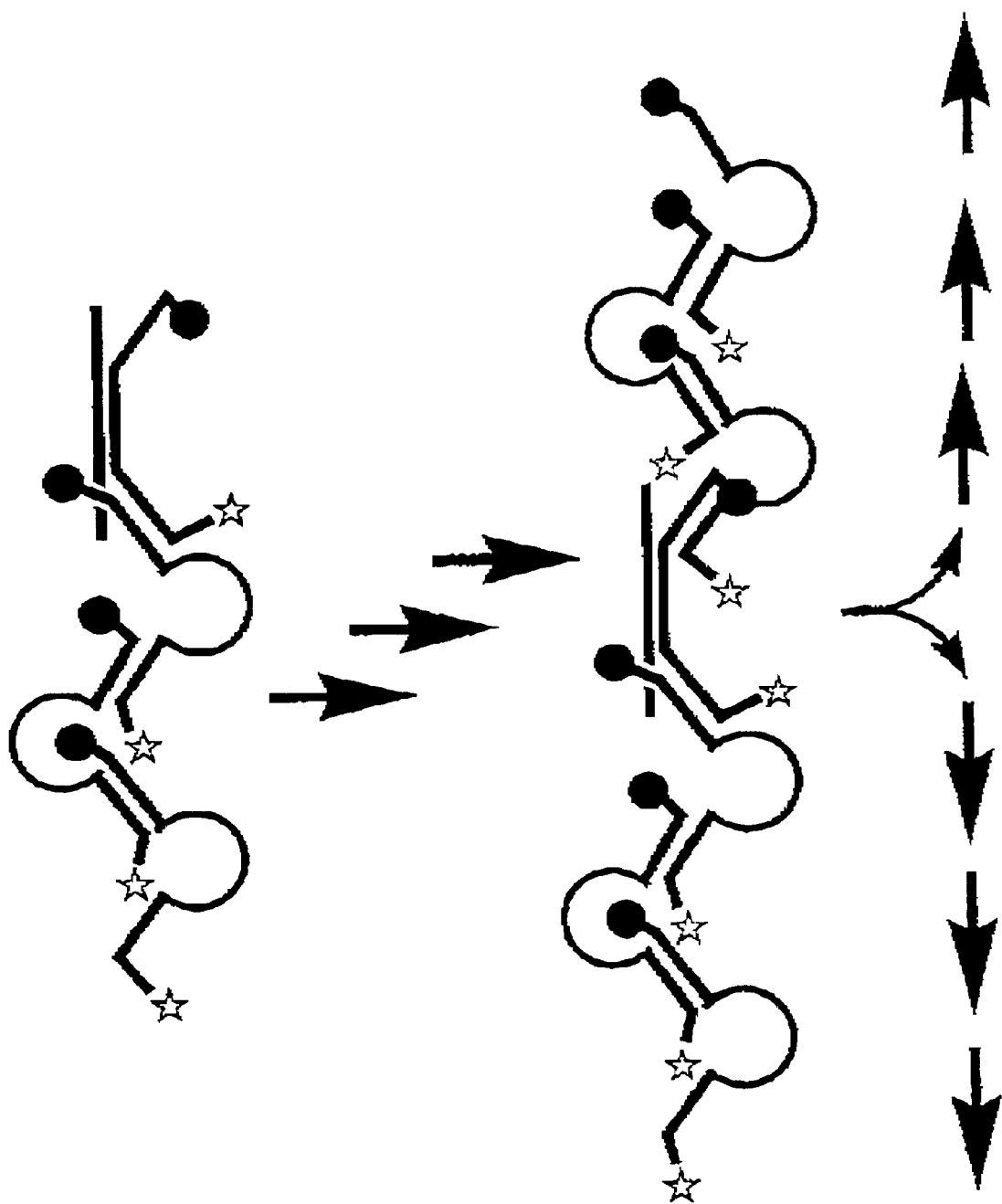
FIG. 11 depicts the bidirectional propagation of the hybridization cascade.

This cascade of hybridization will propagate in both directions (FIG. 11) until one of the nucleic acids becomes depleted from the hybridization mixture. It can therefore be seen that a single hybridization event between the loop sequence of the probe nucleic acid and the target sequence sets off a chain of hybridization reactions between the stem-loop nucleic acids. The formation of the multimolecular complex depends only on the presence of a single copy of the target molecule. Therefore, the cascade hybridization technique provides an exquisitely sensitive method for detecting the presence of a target molecule.

In another embodiment, the nucleic acid that initiates the hybridization cascade comprises a nucleic acid ligand. This ligand or a nucleic acid attached thereto will undergo a conformational change upon binding to a target molecule, which change allows the chain of hybridization to begin. In a preferred embodiment, the nucleic acid ligand will be contained within the loop sequence of a stem-loop nucleic acid. As described above, the initiating event is the energetically-favored binding of the loop sequences to the target molecule, which forces the nucleic acid to adopt a conformation wherein the stem is dissociated. Stem-loop nucleic acids that undergo stem dissociation upon binding to a target molecule are described in U.S. patent application Ser. No. 08/134,028, filed Oct. 7, 1993, entitled "High-Affinity Nucleic Acid Ligands that Discriminate Between Theophylline and Caffeine," now abandoned (see U.S. Pat. No. 5,580,737).

In a related embodiment, the set of nucleic acids will further comprise a nucleic acid with the same sequence as the initial probe nucleic acid, but without the target molecule-binding site. This nucleic acid will therefore not participate in the initial target binding reaction, but will participate in the cascade hybridization. Use of this nucleic acid at a higher concentration than the target-binding nucleic acid will prevent equilibrium exchange of the target molecule between an established multimolecular cascade hybridization product and a free, unhybridized target-binding nucleic acid. This embodiment will prevent the loss of established cascade products from the surface of solid supports (see below).

In any of the preceding embodiments, more than three different nucleic acid sequences may be used, as long as the sequences thereof will promote cascade hybridization.

Although preferred embodiments use intramolecular double-helices and stem-loop nucleic acids, cascade hybridization will also be possible with other nucleic acid structures. All that is required is that the nucleic acids undergo a conformational change upon binding so that sequences previously unavailable for hybridization become available. Any nucleic acid that contains a binding site for a target molecule and undergoes a conformational change when it binds to said target molecule is suitable for use as the cascade-initiating nucleic acid. Any nucleic acids that can bind to said target-bound cascade-initiating nucleic acid and then propagate the cascade as described above are suitable for use as the hybridizing nucleic acids.

Signal Amplification through Cascade Hybridization

In one embodiment, each nucleic acid described above is labeled with an energy transfer pair. The two members of the transfer pair are attached to nucleotides at location on the nucleic acid that are spatially adjacent only when the nucleic acid is not participating in a binding reaction. Therefore, binding of the nucleic acid to either the target molecule or to the other nucleic acids results in the spatial separation of the energy transfer pair. The disruption of energy transfer can be detected by spectroscopic techniques. In the case of the nucleic acids described above with a stem-loop motif, suitable positions for the energy transfer pair members include, but are not limited to, the 5' and the 3' termini of each nucleic acid.

Figure 12:
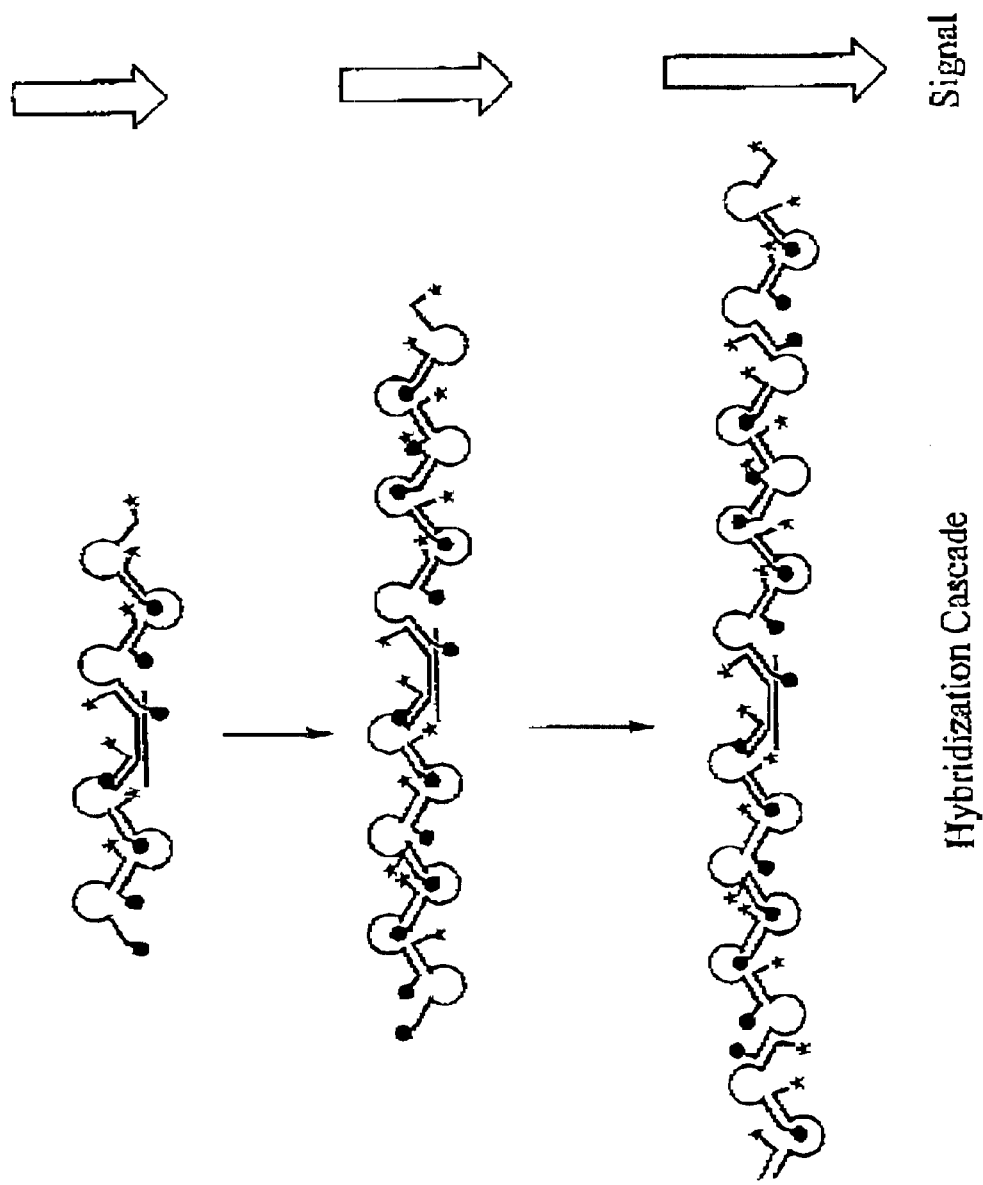
FIG. 12 illustrates how the hybridization cascade is accompanied by the generation of an increasingly large fluorescence signal.

In a preferred embodiment, the energy transfer pair comprises a ligand-beacon. In the unbound conformation, the signal from the fluorescent group is quenched. When the nucleic acid participates in a binding reaction, the fluorescence signal is no longer quenched, and can be detected by any of the means known in the art. Termination of quenching will occur at the initial target molecule binding event, and will also occur at each consequent intermolecular helix formation event. Therefore, the binding of a single nucleic acid to a single target molecule will result in the generation of a fluorescent signal that increases in magnitude as the cascade progresses (FIG. 12). Any energy transfer pair known in the art is suitable for incorporation into the nucleic acids in this embodiment, as discussed above.

Figure 13:
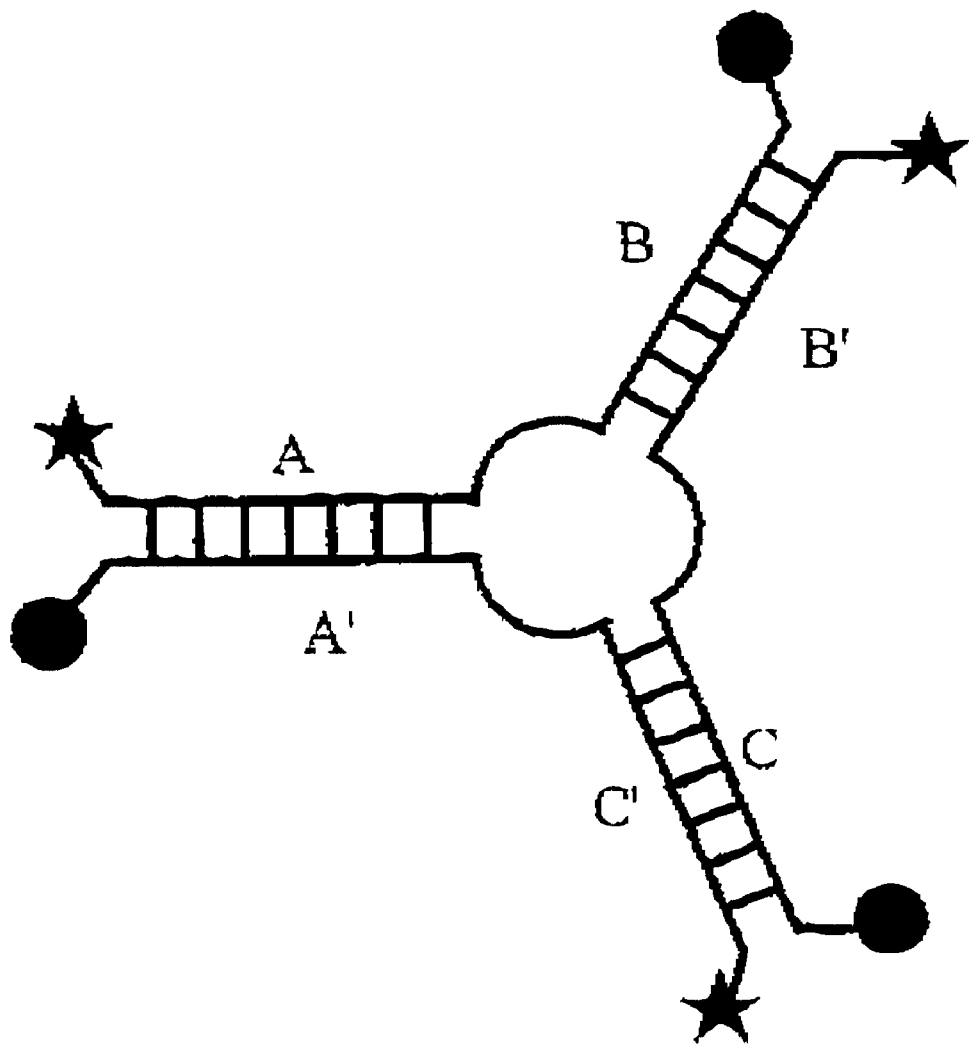
FIG. 13 illustrates that a tri-molecular non-cascade hybridization product will have no fluorescence activity.

One advantage of the energy transfer approach is that only cascade hybridization reactions will lead to the production of a spectroscopically-detectable signal. For example, if the nucleic acids are labeled with a fluorescent group and a quenching group, and if hybridization occurs between the individual nucleic acids in the absence of target molecule-binding, then the individual quenching groups will be spatially adjacent to the fluorescent groups on the hybridizing nucleic acids (FIG. 13) and fluorescent signal will be generated.

In other embodiments, the nucleic acids are labeled with an immunologically detectable probe, such as digoxigenin. The presence of digoxigenin can be detected using fluorescently-labeled antibodies that bind specifically thereto, or by using a sandwich assay.

Use of Cascade Hybridization

In one embodiment, the cascade hybridization system is used to detect the presence of a target molecule in a test solution. A first nucleic acid with a binding site for the target molecule is added to the test solution together with the cascade hybridization nucleic acids described above. If the target molecule is present, then a cascade hybridization complex will form. In one embodiment, this nucleic acid complex will be detected by the standard gel electrophoresis methods known in the art. In another embodiment, the nucleic acids will be labeled with a fluorescent group and a quenching group as described above. The presence of the complex, and hence of the target molecule, can be detected by comparing the fluorescence of the solution with that of a solution containing only the set of nucleic acids.

In another embodiment, the target-binding nucleic acid, containing the binding site for the target molecule, is immobilized on the surface of a solid support, such as a biochip. The nucleic acid is attached at either the 3' or the 5' end to functional groups displayed on the surface of the biochip. Methods for attaching nucleic acids to biochips are well known in the art, and include methods for attaching different nucleic acids to discrete locations on the same biochip. The biochip is then contacted with a test mixture suspected of containing target molecules to which the first nucleic acid can bind. Following removal of unbound material from the biochip by washing, the biochip will be contacted with a solution containing the three sets of nucleic acids labeled as described above with an energy transfer pair. If the biochip-bound nucleic acid binds to target molecule, then a multimolecular complex will form on the biochip. The presence of this complex can be detected by measuring fluorescence on the biochip. Such a biochip can be used to detect exceedingly rare molecules in test mixtures, and will have utility in diagnostic and prognostic medical screening, and in environmental testing.

In a related embodiment, a plurality of different species of target-binding nucleic acids will be localized to discrete locations on the biochip. Each species of target-binding nucleic acid has a unique loop region sequence with a specific affinity for a different target molecule, and a common stem sequence. The biochip is then contacted with a test mixture suspected of containing one or more of the target molecules to which the target-binding nucleic acids can bind. Following incubation with the nucleic acid set, the fluorescence of each location on the biochip is measured. In this way, the presence of multiple target molecules can be determined simultaneously. This method will be useful in medical screening applications, where the diagnosis or prognosis of a particular disease requires the measurement of several different molecules contained in the patient's blood or urine.

Use of Cascade Hybridization in situ

In one embodiment, cascade hybridization is used in situ to give spatial localization data for a target molecule. For example, the location of an RNA molecule in a fixed tissue sample can be determined if the target-binding nucleic acid comprises sequences complementary to this RNA molecule. The use of the fluorescence quenching cascade system in this scenario would result in the formation of a highly fluorescent signal at the site of deposition of the RNA molecule of interest. By using a nucleic acid ligand as the target-binding nucleic acid, the presence of virtually any target molecule can be determined in such fixed specimens. These techniques are vastly more sensitive than the sandwich immunoassays and in situ hybridization techniques known in the art, as the cascade signal amplification system can detect the presence of even a single copy of the target molecule.

Antibody-linked Cascade Hybridization

In a related embodiment, the cascade hybridization system is used to detect the binding of an antibody to a specific target molecule. The antibody is conjugated to an oligonucleotide, and the antibody then used to probe the sample suspected of containing the target molecule of interest. A set of cascade hybridization nucleic acids is then used to detect the presence of the oligonucleotide, and hence the target molecule. The first cascade nucleic acid will hybridize to the antibody-bound oligonucleotide. This cascade nucleic acid will then be available for hybridization with other members of the set of cascade nucleic acids, and cascade hybridization will ensue as described above. If the cascade nucleic acids are fluorescently labeled, or are labeled with both a quenching group and a fluorescent group, then a fluorescent signal will be produced.

This embodiment can be used in situ to give fluorescent localization data for extremely scarce target molecules that would not be detected using the standard sandwich immunoassays known in the art. In particular, the cascade system can be used to detect the binding of even a signal antibody to its target molecule; this sensitivity is not possible using standard immunoassays. This embodiment can also be used in in vitro immunoassays as a replacement for enzyme-linked immunoassays. Alternatively, the nucleic acids can be conjugated to an electron-dense label, such as a gold microparticle, and used in immunoelectron microscopy.

Example 1 describes the synthesis of a ligand beacon to human platelet derived growth factor (PDGF) (see FIG. 3B, SEQ ID NO:2).

Example 2 describes the synthesis of a ligand beacon to thermophilus aquaticus (Taq) DNA polymerase (see FIG. 3B, SEQ ID NO:4).

Example 3 illustrates the use of ligand beacon assays. Two different pairs of aptamers and aptamer-specific ligand beacons were analyzed in this example. A DNA aptamer that binds to the AB-dimer of human platelet-derived growth factor (PDGF) with an equilibrium dissociation constant ($K_d$) of 0.15 nM (Green et al. (1996) Biochemistry 35:14413–14424) was used for the first experiment described in Example 3. This aptamer has the capacity to fold into a three-way helix junction with a three-nucleotide loop at the branch point (FIG. 3A, SEQ ID NO:10). Another DNA aptamer that recognizes DNA polymerase from *Thermus aquaticus* (Taq) polymerase (Dang and Jayasena (1996) J. Mol. Biol. 264:268–278), was used for the second experiment described in Example 3. This aptamer has the potential to fold into a stem-loop structure containing several bulges in the stem (FIG. 3A, SEQ ID NO:9).

Figure 4A:
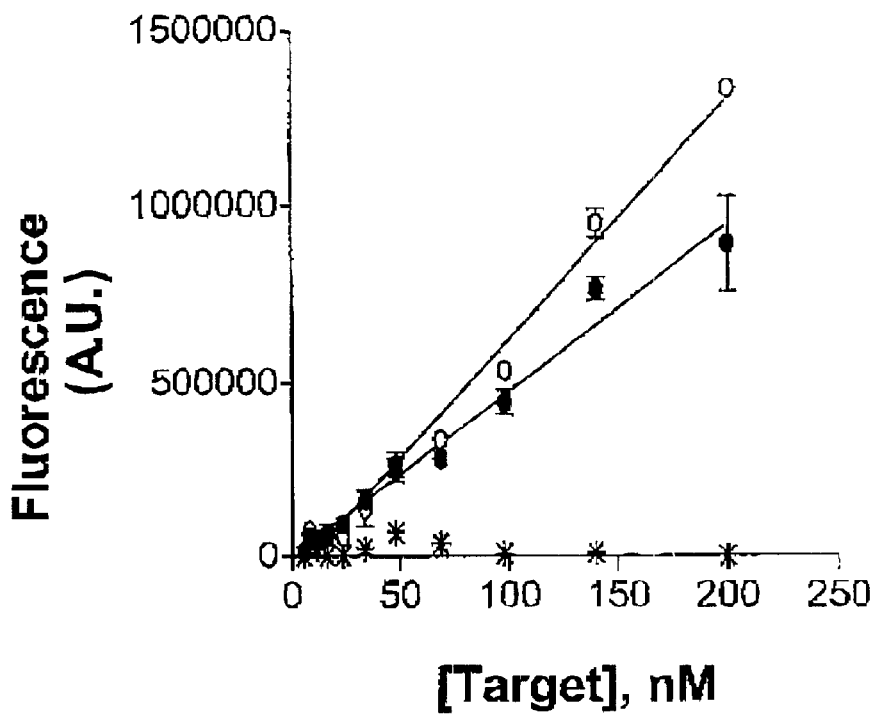
FIGS. 4A and B illustrate the interaction of DNA-based aptamer sequences with ligand beacons. The primary and predicted secondary structures of the aptamers and their corresponding ligand beacon sequences are shown in FIGS. 3A and B. The experimental procedure is described in Example 3.

The results of these assays are set forth in FIGS. 4A and B (PDGF and Taq, respectively), which depicts the fluorescence signal produced by a fixed concentration of ligand beacon in the presence of increasing concentration of an aptamer sequence having a predicted secondary structure. In both cases, the fluorescence signal produced by a fixed amount of ligand beacon increased as the concentration of the appropriate aptamer was increased in the reaction mixture (FIGS. 4A and B; closed circles), indicating that the ligand beacons can have productive interactions with aptamers containing complementary nucleotide regions. In these experiments short single stranded DNA sequences complementary to the loops of the two ligand beacons (FIG. 3B; sequence regions shown in bold) were used as controls. The short sequence complementary to the Taq ligand beacon is single-stranded, whereas the sequence complementary to the PDGF ligand beacon may contain a short base paired region. Both of these short sequences are devoid of extra nucleotides present in aptamers that do not participate in hybridization with ligand beacons. The signal generated by the aptamers (FIG. 4; closed circles) is slightly lower than that produced with the same concentration of the short single-stranded target sequences (FIG. 4; open circles). This result suggests that extra nucleotide regions in aptamers that do not participate in hybridization have very little interference in intermolecular association.

When wrong combinations of aptamer/ligand beacon pairs were mixed, no fluorescence signal above the background level was generated (FIGS. 4A and B; stars), indicating the specificity of aptamer ligand beacon interactions. Moreover, these experiments were carried out in the presence of vast excess of tRNA, further indicating the lack of interference on signal generation by nonspecific nucleic acids. These results, reflecting the extreme specificity of molecular beacons, are consistent with observations made by others (Kostrikis et al. (1998) Science 279:1228–1229; Piatek et al. (1998) Nature Biotechnol. 16:359–363; Tyagi et al. (1998) Nature Biotechnol. 16:49–53; Tyagi and Kramer (1996) Nature Biotecnol. 14:303–308).

The Taq ligand beacon targets a 24 nucleotide stretch of which 22 nucleotides constitute the single stranded loop region in the middle of the Taq aptamer. The hybridization of this pair will result in a continuous duplex containing 24 base pairs, the formation of which might melt the imperfect helix containing 11 base pairs in the aptamer (FIG. 3A). In the case of the PDGF aptamer, hybridization with its ligand beacon is expected to form a duplex with 24 contiguous base pairs at the expense of 9 base pairs found in the aptamer (FIG. 3A). The formation of energetically favored long helical regions with contiguous base pairs is the driving force for the intermolecular hybridization between aptamers and ligand beacons. The results shown in FIG. 4 were obtained upon incubating the aptamer/ligand beacon pairs at 37° C. When incubated at room temperature the amount of fluorescence signal was significantly lower than that observed at 37° C. (data not shown). This suggests that the intermolecular hybridization between the aptamer and its ligand beacon is favored at higher temperature, conditions that enhance fraying or breathing of structured molecules. Overall, these results indicated that an aptamer/ligand beacon pair can be used to develop an assay as illustrated in FIG. 2.

Example 4 describes the synthesis of ligand beacons to human L-Selectin (SEQ ID NO:6) and human P-selectin (SEQ ID NO:8). (see FIG. 3B).

Figure 5A:
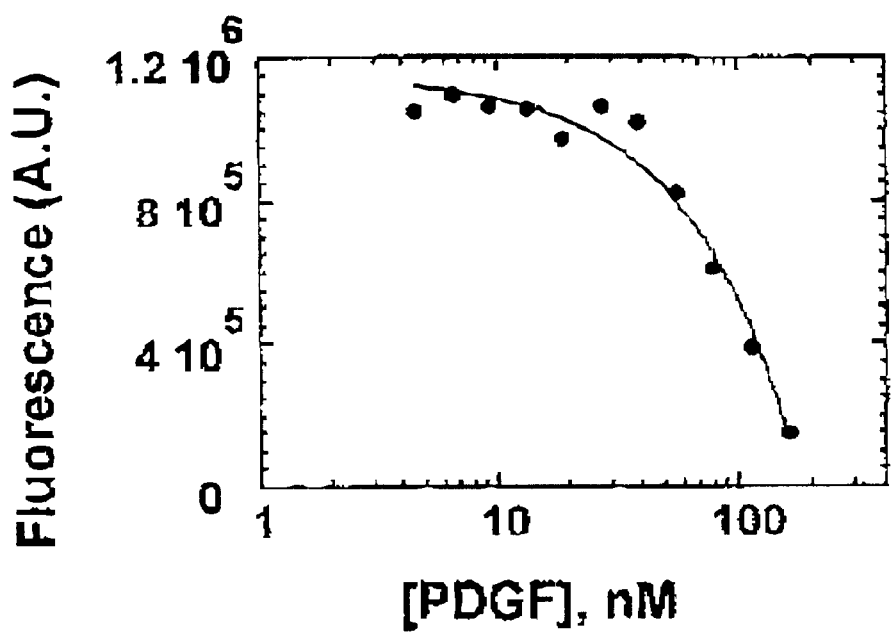
FIG. 5A depicts the results of the ligand beacon assay for PDGF in buffer (Example 5).

Example 5 (FIGS. 5–8) illustrates protein detection using ligand beacon assays in buffer. FIG. 5 depicts the results using PDGF aptamer (SEQ ID NO:10) and its ligand beacon (SEQ ID NO:2) to detect PDGF AB-dimer. As can be seen in FIG. 5A, a decrease in fluorescence signal produced by the same concentration of the ligand beacon was observed with increasing concentration of the PDGF AB-dimer. This result is consistent with the scheme illustrated in FIG. 2. As the concentration of the PDGF protein is increased, increasing amounts of aptamer molecules are sequestered by the protein due to high affinity interaction. As a result, less and less aptamer molecules become available to generate the fluorescence signal upon hybridization with the ligand beacon. In the assay illustrated in FIG. 5A, the PDGF aptamer was first incubated with the PDGF AB-dimer before the ligand beacon was added. No noticeable change in signal was observed 10 minutes or 4 hours after adding the ligand beacon (data not shown), indicating that the excess free ligand beacon present in the reaction did not significantly disturb the equilibrium of aptamer target binding.

Figure 5B:
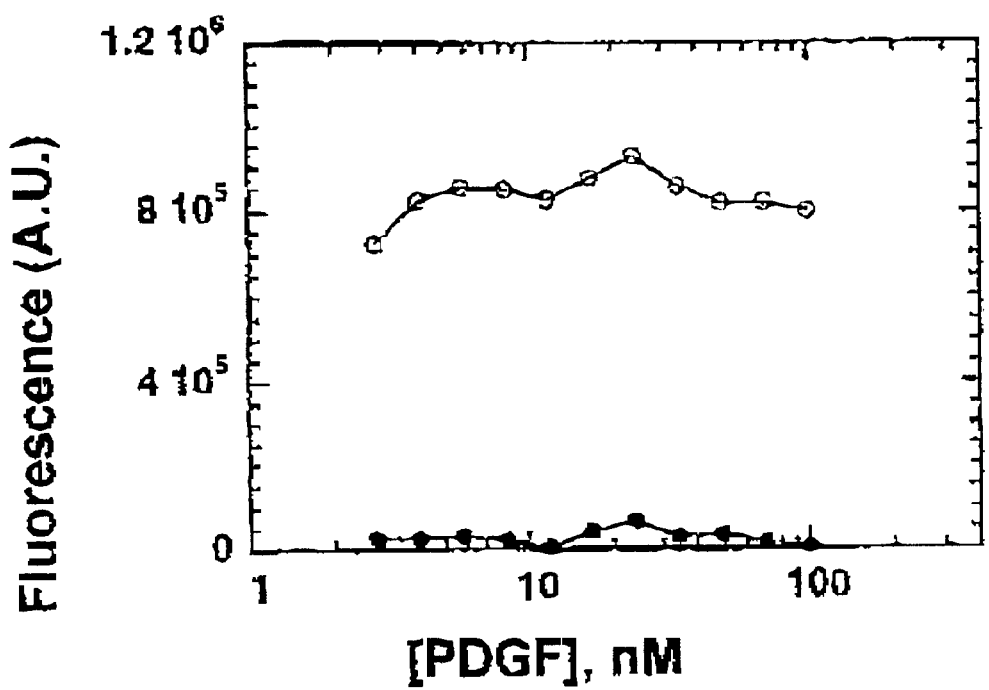
FIG. 5B depicts the results of control experiments carried out in the same buffer at the same temperature.

When the ligand beacon was added to the aptamer before the protein was added no decrease in the fluorescence signal was observed (FIG. 5B, (open circles)). In this case, as expected, the hybridization of the ligand beacon to the aptamer generated a high fluorescence signal. This association between the aptamer and the ligand beacon destroyed the ability of the aptamer to bind to the target. Addition of the target protein to the ligand beacon alone did not change the signal intensity either (FIG. 5B, (closed circles)). Results of these control experiments indicate the following: 1) the decrease in fluorescence signal requires the presence of all three components added in the right order; 2) the decrease in fluorescence signal observed in FIG. 5A is not due to the nonspecific interaction of the fluorophore with the protein that might have caused the quenching of fluorescence; 3) the native or the functional conformation of an aptamer must be preserved at the time of its interaction with its target; and 4) as was expected, the stability of the ligand beacon aptamer hybrid is such that the addition of the target protein was unable to dissociate the aptamer from the hybrid.

Figure 6:
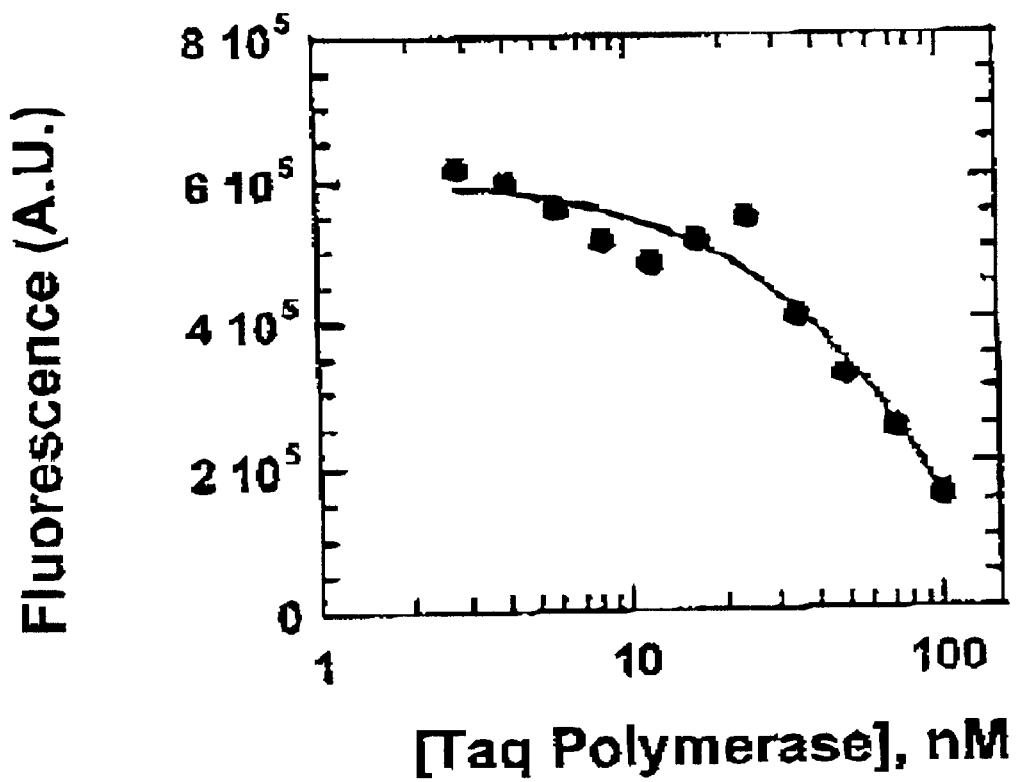
FIG. 6 depicts the results of the ligand beacon assay for Taq polymerase in buffer.

Similar to the results obtained with the PDGF protein and its aptamer/ligand beacon pair, a decrease in fluorescence signal with the increasing concentration of Taq DNA polymerase added to its aptamer/ligand beacon pair was also observed (FIG. 6). The results of these experiments are consistent with the proposed scheme for the ligand beacon assay.

The assay concept was further tested with two different, but closely related proteins; human L-selectin and human P-selectin. High affinity aptamers to these two human selectins have been recently described (Jenison et al. (1998) Antisense & Nucleic Acids Drug Dev. 8:265–279; O'Connell et al. (1996) Proc. Natl. Acad. Sci. USA 93:5883–5887). The DNA aptamer that binds to L-selectin with a $K_d$ of 1.8 nM has the potential to fold into a stem-loop structure with an internal bulge (FIG. 3A, SEQ ID NO:11). For P-selectin, an RNA aptamer was chosen to test the feasibility of an RNA aptamer in the assay. The P-selectin RNA aptamer containing 2'-F pyrimidines has the potential to form a stem-loop structure with several internal bulges (FIG. 3A, SEQ ID NO:12). The interaction of this particular aptamer with P-selectin has a $K_d$ of 40 pM. Ligand beacons specific to both aptamers were designed (FIG. 3B, SEQ ID NOS:6 and 8, respectively).

Figure 7A:
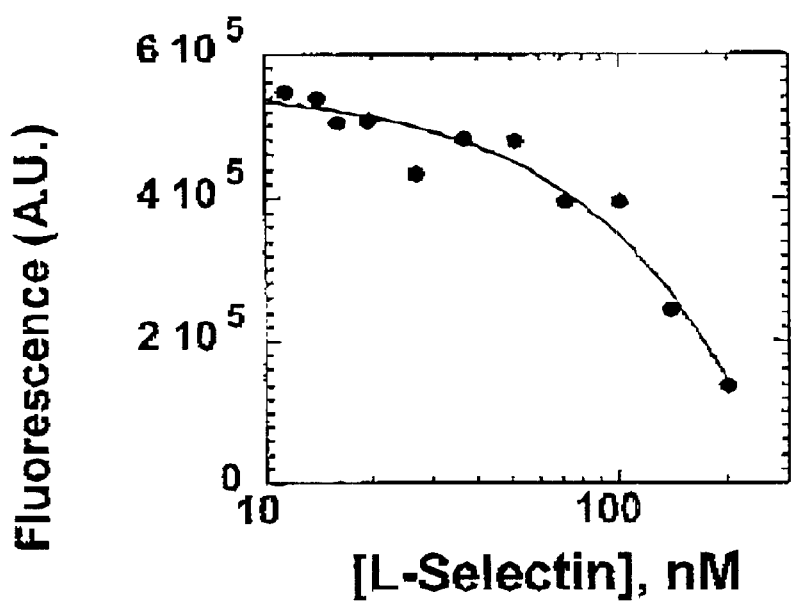
FIGS. 7A and 7B depict the results of the ligand beacon assay for human L-selectin in buffer.
Figure 7B:
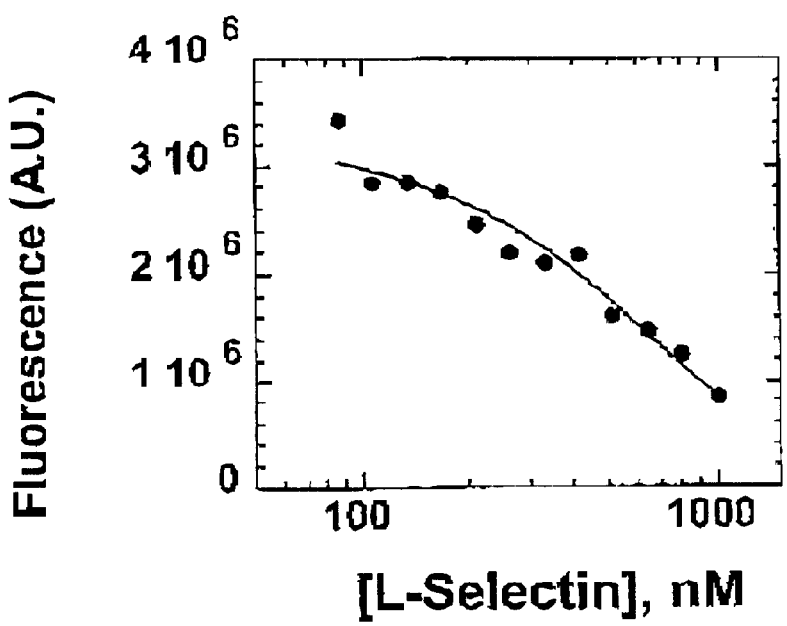

Analogous to PDGF and Taq aptamer/ligand beacon pairs, the L-selectin aptamer/ligand beacon pair also showed productive hybridization at 37° C. producing a fluorescence signal (data not shown), indicating the feasibility of using this pair in the assay. Additionally, as in the case of the PDGF and Taq proteins, the fluorescence signal measured was inversely proportional to the amount of L-selectin added (FIG. 7A). In the L-selectin assay, as well as in the PDGF assay, the fluorescence signal approaches zero when the target concentration approaches the concentration of the aptamer, suggesting that the concentration of the aptamer must be increased to detect high concentrations of the target. By increasing the aptamer and the ligand beacon concentration, it is possible to detect high concentrations of the target (FIG. 7B). Hence, the range of the assay is dictated by the concentration of the aptamer/ligand beacon pair.

Figure 8A:
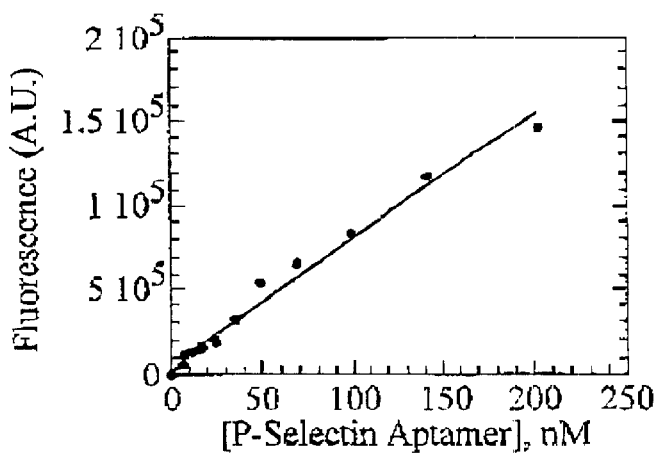
FIG. 8A illustrates the interaction of the RNA based P-selectin aptamer sequence with its ligand beacon.
Figure 8B:
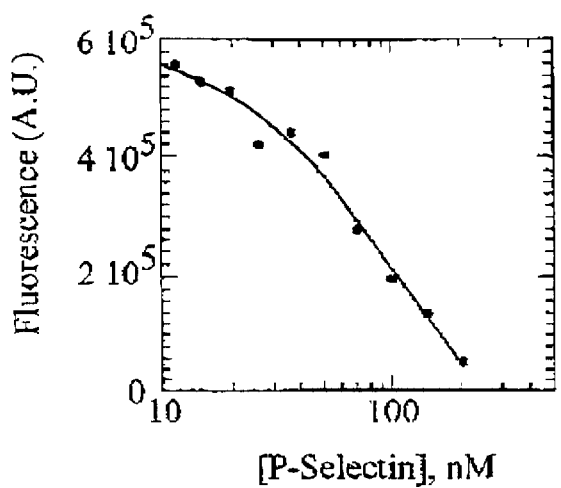
FIG. 8B depicts the results of the ligand beacon assay for human P-selectin.
Figure 8C:
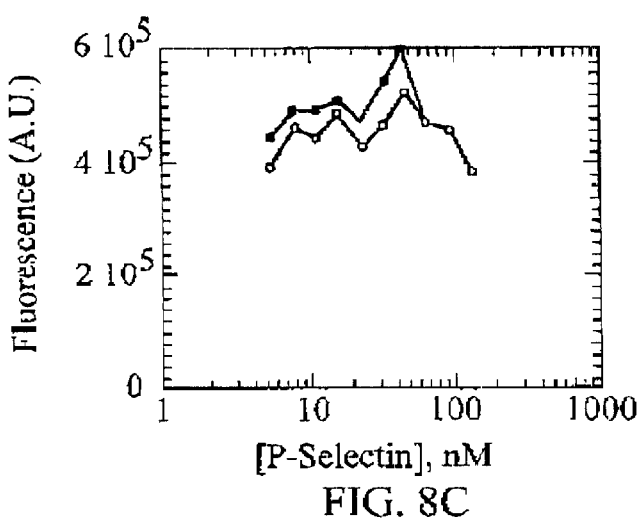
FIG. 8C illustrates the specificity of the assay with respect to the similar proteins L-selectin and P-selectin.

Example 5 also illustrates the use of a 2'-F-pyrimidine-containing RNA aptamer specific for human P-selectin in a ligand beacon assay. Similar to DNA aptamers, the 2'-F-pyrimidine containing RNA aptamer was able to hybridize efficiently to its ligand beacon at 37° C. to generate fluorescence signal in a concentration dependant manner (FIG. 8A). Furthermore, it was also possible to detect human P-selectin using this aptamer/ligand beacon pair (FIG. 8B). The results of the assay based on an RNA aptamer to detect the P-selectin protein follows the same trend as the assays based on DNA aptamers, indicating that both DNA and RNA aptamers are equally suited for the ligand beacon assay. The specificity of the assay was also tested by exchanging the two closely related target proteins, L-selectin and P-selectin. As shown in FIG. 8C, there was no significant decrease in the fluorescence signal when an increasing concentration of the wrong selectin was added to a matched pair of aptamer/ligand beacon; for example, P-selectin protein with L-selectin aptamer and L-selectin ligand beacon. These results indicate that the assay specifically detects the correct target in the medium. Although specific interactions between all three components, the target, the aptamer and the ligand beacon are crucial, by and large, the overall specificity of the assay rests primarily upon the aptamer-target interaction. Nonspecific sequestering of the aptamer could also lead to the decrease in fluorescence signal. The lack of cross reactivity in the two selectin assays is primarily due to the specificity of aptamers that were selected to recognize the two selecting.

L-selectin and P-selectin, together with E-selectin, constitute a family of homologous cell adhesion molecules called selecting. Although these three selectins are highly homologous, aptamers that have been selected to bind one type do not bind the other two types with high affinity. The L-selectin DNA aptamer used in this assay discriminates its binding to P-selectin and E-selectin by 9000-fold and 300-fold, respectively (O'Connell et al. (1996) Proc. Natl. Acad. Sci. USA 93:5883–5887). The P-selectin RNA aptamer used in this study exhibits 2000-fold reduced affinity to L-selectin (Jenison et al. (1998) Antisense & Nucleic Acids Drug Dev. 8: 265–279). This high level of discrimination in target binding by the aptamers translated to the observed specificity in the ligand beacon assay.

Example 6 illustrates the feasibility of using a ligand beacon assay to measure protein targets in plasma. Biological fluids are complex mixtures made up of constituents that generally tend to interfere in diagnostic assays. To avoid such interference, certain diagnostic assay formats, such as enzyme-linked immunosorbent assays (ELISA), include a step that captures (or separates) the analyte of interest from biological fluids before being detected. Homogeneous assays, however, are able to detect analytes even in complex milieu of biological fluids, without a need for separation of analytes. Hence, homogeneous assays are simple to use, attractive for high throughput applications and less expensive. Example 6 demonstrates that the ligand beacon assay allows homogeneous detection of proteins directly in plasma, making the assay more attractive for clinical diagnostic applications.

Figure 9A:
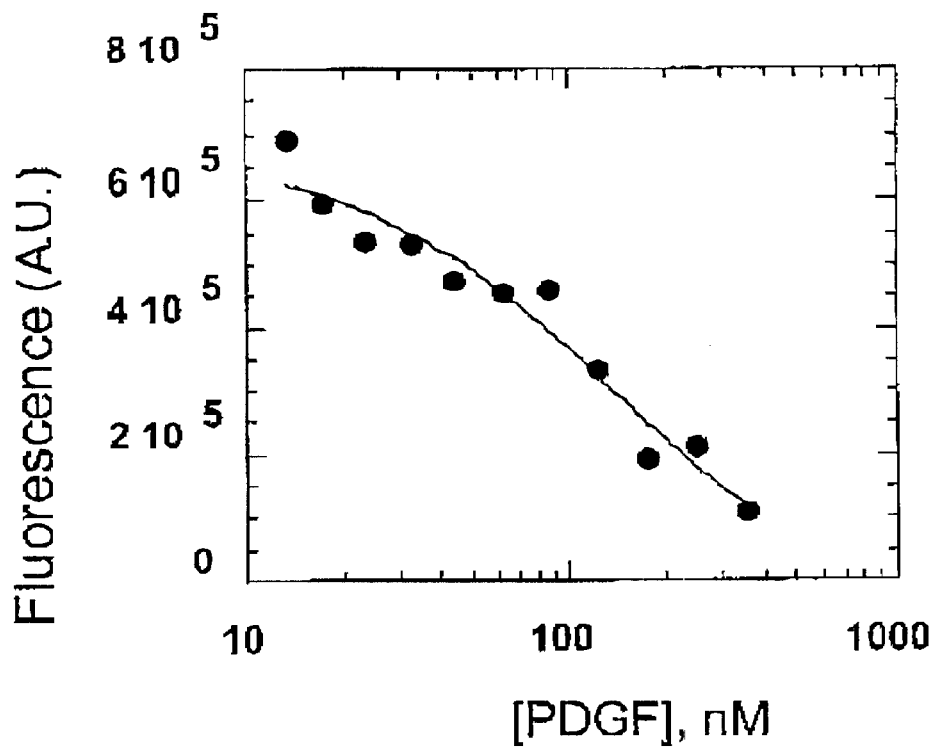
FIGS. 9A–9C depict the results of ligand beacon assays for detecting proteins in plasma.
Figure 9B:
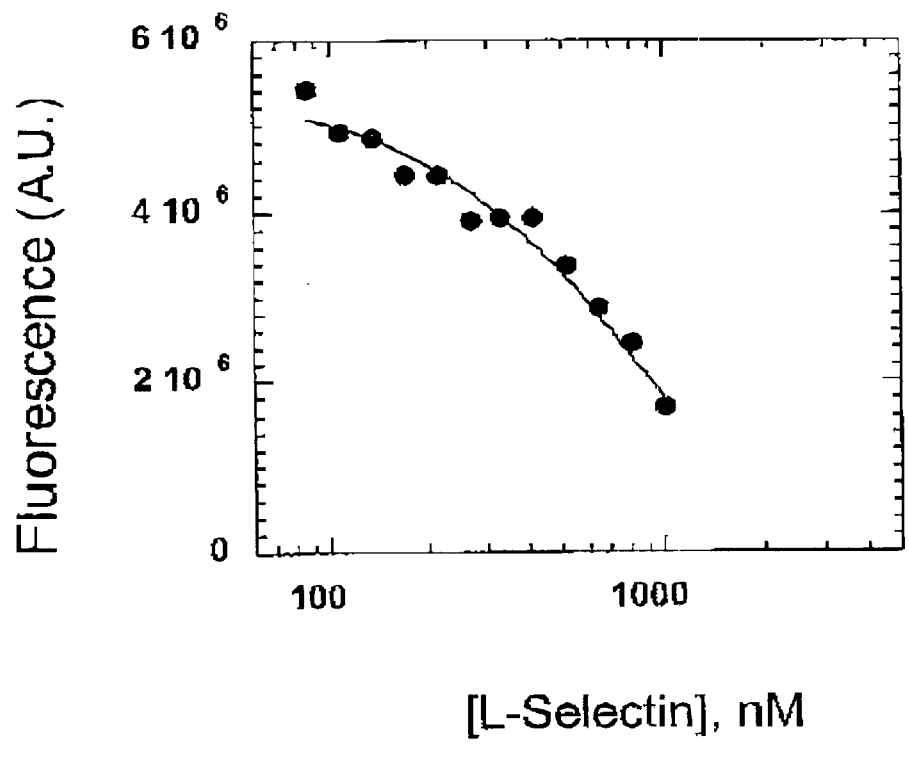
Figure 9C:
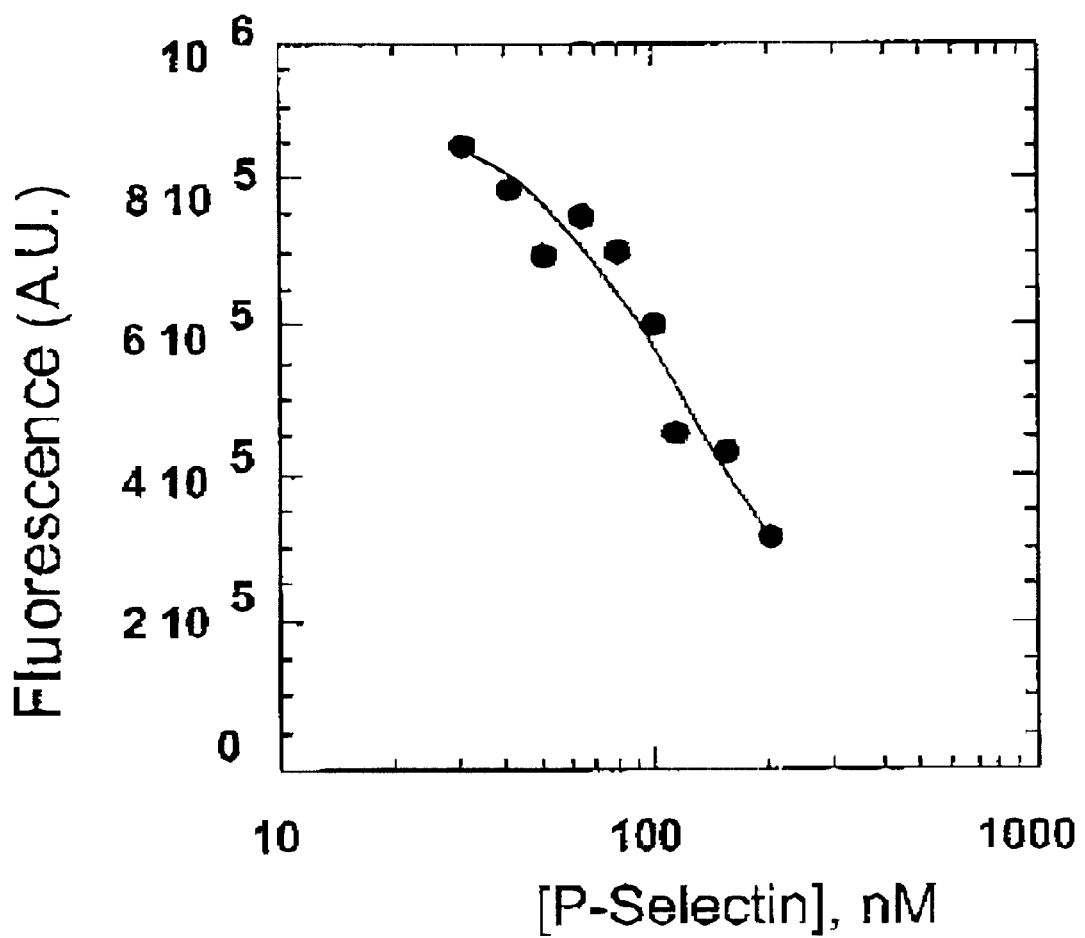

In Example 6, the target protein was added to human plasma containing the aptamer mixed with tRNA. After incubating the reaction mixture for 10 minutes at 37° C., the corresponding ligand beacon was added and the incubation was continued for another 10 minutes before fluorescence was measured. As shown in FIGS. 9A–C, all three protein targets could be measured in human plasma. In each case, the decrease in fluorescence signal observed in plasma in response to the increase in target protein concentration is analogous to what was observed in the buffer. Plasma contains a variety of proteins and other metabolites at varying concentrations. Most importantly, these components did not appear to interfere with the overall performance of the assay. Analogous to the assay carried out in the buffer, the detection range of the assay in plasma was also dictated by the concentration of the aptamer/ligand beacon pair. The use of two different concentrations of aptamer/ligand beacon pairs enabled detection of two different concentrations of target proteins (data not shown). The ability to detect protein targets in plasma using the ligand beacon assay would be expected to expand its utility.

Example 7 illustrates cascade hybridization.

The following examples are presented for illustrative purposes only and are not intended to limit the scope of the invention.

EXAMPLES

Methods and Materials

DNA oligonucleotide sequences were synthesized by standard solid phase chemical synthesis using cyanoethyl phosphoramidites and purified on polyacrylamide gels run under denaturing conditions. The 2'-F-pyrimidine containing RNA aptamer was produced by run-off in vitro transcription method using T7 RNA polymerase and a PCR-derived DNA template (Milligan et al. (1987) Nucleic Acids Res. 15:8783–8798) as described (Davis et al. (1998) Nucleic Acids Research 26:3915–3924). The AB-dimer of the human platelet-derived growth factor (PDGF-AB), human L- and P-selectin were purchased from R & D Systems. Taq DNA polymerase was obtained from Roche Molecular Systems.

Ligand beacon sequences containing fluorescein at the 5' end were synthesized using fluorescein phosphoramidite (Glen Research). The solid phase synthesis of ligand beacons was initiated with 3'-amino-modifier C7 CPG (Glen Research) that incorporates reactive amine functional groups at 3' ends to facilitate post-synthesis attachment of the quencher, 4-(4'-dimethylaminophenylazo)benzoic acid (DABCYL) (Tyagi and Kramer (1996) Nature Biotecnol. 14:303–308). After deprotection, the ligand beacons were equilibrated in 300 μL of 0.3 M sodium acetate at 3–5 mg/mL and incubated for 30–60 minutes at room temperature, then precipitated with ethanol. The DNA pellet was then dissolved in 100 μL of 100 mM sodium borate buffer (pH 9.3) and mixed with 10 mg of succinimidyl ester of DABCYL (Molecular Probes) in 100 μL of anhydrous N, N-dimethyl formamide (DMF). The DABCYL conjugation reaction was allowed to proceed for 30 minutes at room temperature. The reaction mixture was then passed through Centrex U-0.5 10K MWCO Centrifugal Ultrafiltration Unit (Schleicher and Schuell) and the DNA retained on the filter was thoroughly washed with DMF. DNA-DABCYL conjugate was recovered from the filter and purified on 10% polyacrylamide gels ran under denaturing conditions. Ligand beacons (10–50 μM) in the appropriate assay buffer were heated to 90° C. and allowed to cool to room temperature before use.

Alternatively, after deprotection, the oligonucleotide was equilibrated 100 mM sodium borate buffer (pH 9.3) at 4 mg/mL and mixed with an equal volume of the succinimidyl ester of (4-dimethylaminophenylazo)benozoic acid (DABCYL) in anhydrous DMF (5 mg/100 μL). The reaction was allowed to proceed for 30 minutes at room temperature. Unreacted DABCYL was removed from the derivatized oligonucleotide by passing the reaction mixture through a 5000 MW cutoff Centricon filter. Subsequently, derivatized oligonucleotide was purified by gel electrophoresis under denaturing conditions. The ligand beacon was heated to 80° C. in PBSM buffer (10.1 mM $Na_2HPO_4$, 1.8 mM $KH_2PO_4$, 137 mM NaCl, 2.7 mM KCl, 1 mM $MgCl_2$, (pH 7.4)) and slowly cooled to room temperature before use.

Aptamer-Ligand Beacon Interaction

A fixed concentration (200 nM) of a ligand beacon was mixed with increasing concentration of the corresponding aptamer in 100 μL volume of the binding buffer containing 4 μM tRNA in a microtiter plate and incubated at 37° C. for 10 minutes before fluorescence signal was measured. Fluorescence was measured at 530 nm after exciting at 488 nm monochromatic laser light in 96-well format Vistra Fluorimager SI instrument.

Ligand Beacon Assay

Aptamers at 10 μM concentration in the appropriate binding buffer were heated to 90° C. and cooled to room temperature to facilitate secondary structure formation. Serially diluted target protein (50 μL) either in the appropriate buffer or in plasma were added to microtiter plate wells in duplicate. Then, a fixed concentration of an aptamer mixed with tRNA at a concentration of four-fold higher than that of the aptamer in 25 μL volume was added to each well. After 10 minutes incubation at 37° C., 25 μL of the corresponding ligand beacon was added to the final concentration equivalent to that of the aptamer and the incubation was continued for another 10 minutes. Fluorescence in each well was measured at 530 nm after exciting at 488 nm using monochromatic laser light in a 96-well format Vistra Fluorimager SI.

The fluorescence signal intensity of each well was subtracted from that of a background well that contained only the ligand beacon in the appropriate buffer or plasma. The background-subtracted signal was plotted against the log concentration of the target protein. Nonlinear least squares method was used for curve fitting with Kaleidagraph (Synergy Software, Reading, Pa.) using equation 5 as derived below.

$$P + A \rightleftharpoons P:A \quad [1]$$

$$K_a = \frac{[P:A]}{[P][A]}$$

$$[P_T] = [P] + [P:A]$$

$$[A_T] = [A] + [P:A]$$

$$[P:A] = K_a[P][A]$$

Where, $K_a$ is the equilibrium association constant for the interaction between the target protein P and the aptamer A. $P_T$ represents the total protein concentration and $A_T$ indicates the total aptamer concentration. Equation 1 can be rearranged to obtain Equation 2.

$$[P:A] = K_a([P_T]-[P:A])([A_T]-[P:A])$$

$$[P:A] = K_a([P_T][A_T]-[P:A]([A_T]+[P_T])+[P:A]^2)$$

$$[P:A]^2-[P:A]([A_T]+[P_T]+K_a^{-1})+([P_T][A_T])=0 \quad [2]$$

Equation 2 has the general form:

$$x^2 - bx + c = 0$$

Hence, $$[P:A] = \frac{([A_T] + [P_T] + K_d)}{2} \sqrt{\frac{([A_T] + [P_T] + K_d)^2}{4} - [P_T][A_T]} \quad [3]$$

$$\text{Where, } K_a = \frac{1}{K_d}$$

Free aptamer interacts with the ligand beacon B, to generate the complex AB* that produces the fluorescence signal.

$$A + B \rightarrow A:B^{**} = \text{Fluorescence signal}$$

$$[A:B^*] = [A] = [A_T] - [P:A] \quad [4]$$

Using Equation 3, $$\text{Signal} = [A_T] - \quad [5]$$

$$\left[ \frac{([A_T] + [P_T] + K_d)}{2} - \sqrt{\frac{(([A_T] + P_T] + K_d))^2}{4} - [P_T][A_T]} \right]$$

Example 1
Ligand Beacon for Use with PDGF Nucleic Acid Ligand

A nucleic acid ligand to human platelet derived growth factor (PDGF) with the following sequence was obtained using the SELEX process as described above:

5'-tgggagggcgcgttcttcgtggttacttttagtcccgt-3' (SEQ ID NO:1)

The sequence in bold was used to design a ligand beacon with the following sequence:

5'-F-gcgagaaagtaaccacgaagaagaacgcgcccctcgc-Q-3' (SEQ ID NO:2)

wherein the bold sequence in the ligand beacon is complementary to the bold sequence in the nucleic acid ligand, and the underlined sequences form the stem. The ligand beacon was labeled with fluorescein (F) at the 5' terminus and DABCYL (Q) at the 3' terminus as described above.

Example 2
Ligand Beacon for Use with Nucleic Acid Ligand to TAQ Polymerase A nucleic acid ligand to *Thermophilus aquaticus* (TAQ) DNA Polymerase with the following sequence was obtained through the SELEX methodology as described above:

5=-tggcggagcgatcatctcagagcattcttagcgttttgttcttgtgtatga-3' (SEQ ID NO:3)

The sequence in bold above was used to design a ligand beacon with the following sequence:

5'-F-gcgagcaagaacaaaacgctaagaatgctctcgc-Q-3' (SEQ ID NO:4)

wherein the bold sequence in the ligand beacon is complementary to the bold sequence in the nucleic acid ligand, and the underlined sequences form the stem. The ligand beacon was labeled with fluorescein at the 5' terminus and DAB-CYL at the 3' terminus as described above.

Example 3
Specificity of Ligand Beacon Interaction with Nucleic Acid Ligand In order to test the specificity of the interactions of the ligand beacons with their cognate nucleic acid ligands, the TAQ ligand beacon and the PDGF ligand beacon were contacted with either: their cognate nucleic acid ligand, a twenty nucleotides-long linear template oligonucleotide sequence that is complementary to the ligand beacon, or a non-cognate nucleic acid ligand. The results are shown in FIGS. 4A and B. In the example shown in FIG. 4A, 200 nM PDGF-ligand beacon was mixed with increasing concentration of PDGF nucleic acid ligand (closed circles), 20-nt linear PDGF template (open circle) or TAQ nucleic acid ligand (asterisks) in PBSM buffer consisting of 10.1 mM Na$_2$HPO$_4$, 1.8 mM KH$_2$PO$_4$, 137 mM NaCl, 2.7 mM KCl, 1 mM MgCl$_2$, 4 μM tRNA (pH 7.4) and incubated at 37° C. for 10 minutes before fluorescence was measured. Fluorescence was measured at 530 nm after exiting at 488 nm using monochromatic laser light in 96-well format Vistra fluorimager SI. Each experiment was done in duplicate.

Figure 4B:
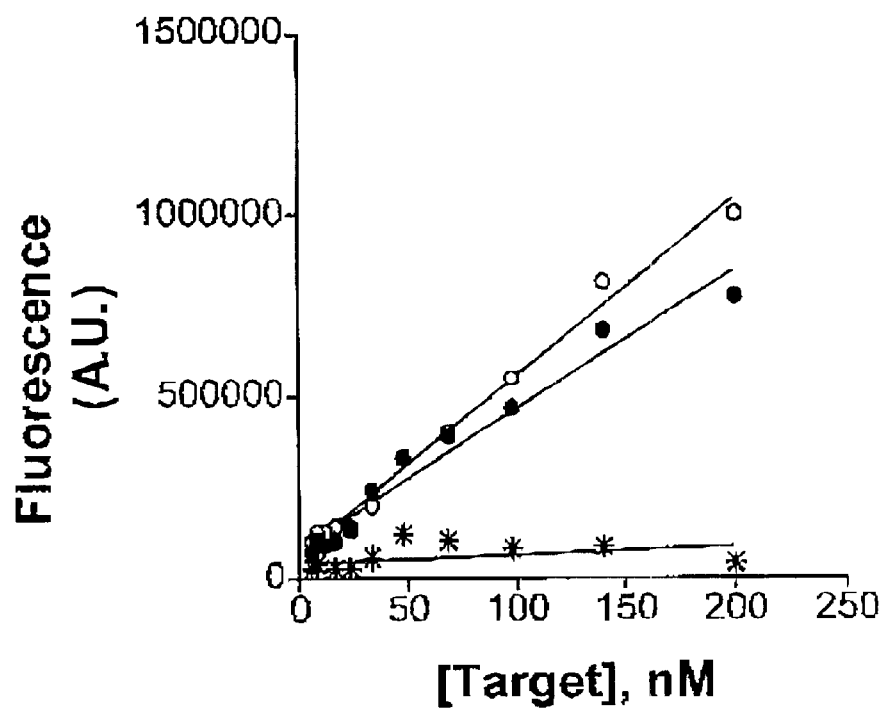
FIG. 4B depicts the results of the interaction of Taq aptamer with its ligand beacon. Closed circles indicate the signal generated by the ligand beacon specific to the Taq aptamer upon interaction with the Taq aptamer with predicted stem-loop structure. Open circles represent the signal generated by the same ligand beacon when incubated with the truncated sequence (indicated in bold in FIG. 3A) without the extra nucleotides in the aptamer. Stars indicate the signal generated by the same ligand beacon when mixed with the PDGF aptamer.

In the example shown in FIG. 4B, 200 nM TAQ-ligand beacon was mixed with increasing concentration of TAQ nucleic acid ligand (closed circles), 20-nt linear TAQ template (open circle) and PDGF nucleic acid ligand (asterisks) in PBSM buffer containing 4 μM tRNA and incubated at 37° C. for 10 minutes before fluorescence was measured. Each experiment was done in duplicate.

Figure 4C:
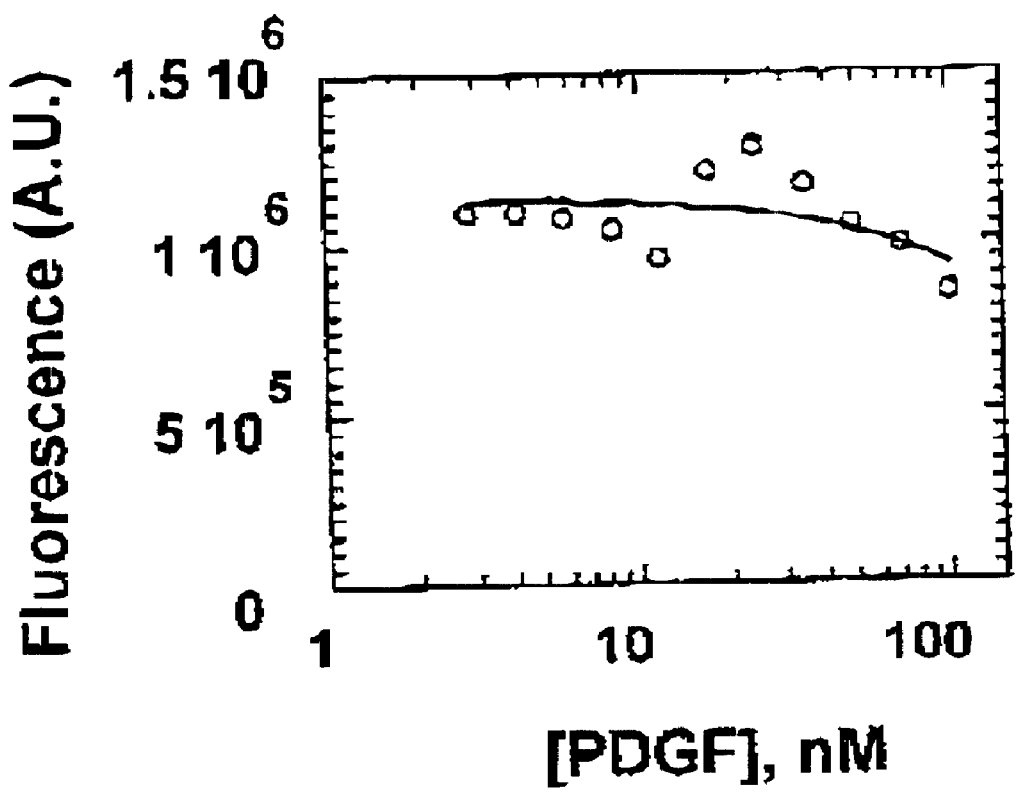
FIG. 4C illustrates the extent to which the change in fluorescence emission is dependent on the presence of a specific target. In this case, no change in fluorescence emission is observed when a nucleic acid ligand to Taq polymerase and its cognate ligand beacon are mixed with PDGF.

In the example shown in FIG. 4C, TAQ-nucleic acid ligand (100 nM) was mixed with increasing concentrations of PDGF in PBSM buffer containing 4 μM tRNA at 37° C. for 10 minutes. Then 110 nM TAQ-ligand beacon was added, incubated for an additional 10 minutes at the same temperature and fluorescence was measured. As illustrated in FIG. 4C, no concentration-dependent signal reduction is observed when the wrong target protein is added. These results illustrate that signal generation is specific for the target protein.

Example 4
Ligand Beacons and Nucleic Acid Ligands to Selectins

Ligand beacons were synthesized for P-selectin and L-selectin nucleic acid ligands. The sequences of the appropriate nucleic acid ligands and their cognate ligand beacons are given below:

L-Selectin Nucleic Acid Ligand

5'-tagccaaggtaaccagtacaaggtgctaaacgtaatggcttcggcttac-3' (SEQ ID NO:5)

L-Selectin Ligand Beacon

5'-F-gcgagtgtactggttaccttggctactcgc-Q-3' (SEQ ID NO:6)

P-Selectin Nucleic Acid Ligand

5'-cucaacgagccaggaacaucgaggucagcaaacgcgag-3' (SEQ ID NO:7)

P-Selectin Ligand Beacon

5'-F-gcgagctcgcgtttgctgacgtcgactcgc-Q-3' (SEQ ID NO:8)

wherein the L-Selectin nucleic acid ligand is a 49-mer single-stranded DNA, and the P-Selectin nucleic acid ligand is a 38-mer RNA molecule containing 2'-F-substituted pyrimidines. The F represents fluorescein and Q represents DABCYL. As in the previous examples, the ligand beacons were synthesized with fluorescein at the 5' end, and a free amino group at the 3' end. The free amino group was reacted with the succinimidyl ester of DABCYL in order to position DABCYL at the 3' end of the ligand beacon.

Example 5
Protein Detection Using Ligand Beacon Assays
PDGF AB-Dimer The PDGF ligand beacon was used in an assay in which 160 nM PDGF nucleic acid ligand (SEQ ID NO:1) was mixed with an increasing concentration of PDGF AB-dimer in PBSM buffer [10.1 mM Na$_2$HPO$_4$, 1.8 mM KH$_2$PO$_4$, 137 mM NaCl, 2.7 mM KCl, 1 mM MgCl$_2$, 4 μM tRNA (pH 7.4)] for 10 minutes at 37° C. Then, ligand beacon (SEQ ID NO:2) was added to a final concentration of 160 nM and the mixture was incubated for 10 minutes at 37° C. A measurement of fluorescein emission at 530 nm was made for each concentration of PDGF using 488 nm monochromatic laser light for excitation in a 96 well format Vistra Fluorimager SI. The average value of fluorescence signals derived from duplicates was plotted against the corresponding log concentration of the concentration PDGF AB-dimer in nanomoles. The results are displayed in FIG. 5A.

Control experiments carried out in the same buffer and temperature, the results of which are displayed in FIG. 5B. Open circles represent the fluorescence signal obtained when the 100 nM PDGF aptamer was first incubated with 100 nM PDGF ligand beacon before the protein was added. Closed circles indicate the signal generated when 100 nM PDGF ligand beacon was mixed with increasing concentration of the PDGF AB-dimer in the absence of the aptamer.
TAQ DNA Polymerase An assay using constant concentrations of TAQ nucleic acid ligand and TAQ ligand beacon, and varying concentrations of TAQ DNA polymerase, was carried out as described above. Again, the fluorescence emission decreased with increasing amounts of the ligand Taq Polymerase. The results are shown in FIG. 6.
Human L-Selectin A fixed concentration of L-selectin aptamer was mixed with increasing concentration of human L-selectin in SHMCK buffer [20 mM HEPES, 120 mM NaCl, 5 mM KCl, 1 mM $MgCl_2$, 1 mM $CaCl_2$, 4 µM tRNA, (pH 7.4)] and incubated for 10 minutes at 37° C. Then, L-selectin ligand beacon was added to a final concentration equivalent to that of the aptamer, incubated additional 10 minutes at 37° C. and fluorescence was measured. The results are depicted in FIGS. 7A and B. It can be seen that the dynamic range of the assay can be easily varied by changing the concentration of the nucleic acid ligand/ligand beacon pair.
Human P-Selectin P-selectin ligand beacon (200 nM) was mixed with increasing concentration of the P-selectin RNA aptamer in SHMCK buffer [20 mM HEPES, 120 mM NaCl, 5 mM KCl, 1 mM $MgCl_2$, 1 mM $CaCl_2$, 4 µM tRNA, (pH 7.4)] and incubated for 10 minutes at 37° C. The fluorescence signal was then measured as described above. The results are depicted in FIG. 8A.

P-selectin aptamer (200 nM) was mixed with increasing concentration of human P-selectin in SHMCK buffer [20 mM HEPES, 120 mM NaCl, 5 mM KCl, 1 mM $MgCl_2$, 1 mM $CaCl_2$, 4µM tRNA, (pH 7.4)] and incubated for 10 minutes at 37° C. Then, P-selectin ligand beacon was added to a final concentration of 200 nM, incubated for additional 10 minutes at 37° C. and fluorescence was measured. The results are depicted in FIG. 8B.

In order to demonstrate the specificity of the ligand beacon/nucleic acid ligand interaction, an assay was performed in which the P-Selectin nucleic acid ligand was mixed with its cognate ligand beacon and L-Selectin. Specifically, L-Selectin nucleic acid ligand (200 nM) was mixed with increasing concentrations of P-Selectin in SHMCK buffer containing 4 µM tRNA. The mixture was incubated at 37° C. for 15 minutes. Then 220 nM L-Selectin ligand beacon was added and the mixture was incubated an additional 10 minutes at the same temperature and fluorescence was measured (FIG. 8C; (•)). P-Selectin nucleic acid ligand (200 nM) was mixed with increasing concentrations of L-Selectin in SHMCK buffer containing 4 µM tRNA at 37° C. for 15 minutes. Then 220 nM P-Selectin ligand beacon was added, incubated for an additional 10 minutes at the same temperature and fluorescence was measured (FIG. 8C; (○)).

As can be seen from the results shown in FIG. 8C, there is a little or no change in the fluorescence intensity when the wrong Selectin is added. In the presence of the wrong target protein the nucleic acid ligand is available for binding to the ligand beacon resulting in high fluorescence. This result indicates that the change in fluorescence is dependent on the presence of the specific target.

Example 6

Use of Ligand Beacons Assays in Plasma

Proteins resuspended in appropriate buffers were added to freshly prepared plasma such that the plasma concentration was not less than 80% (v/v). To these solutions 10 µL of an aptamer mixed with tRNA in a binding buffer (PBSM or SHMCK) was added such that the final concentration of aptamers was either 200 nM or 800 nM (for L-selectin) and the final concentration of tRNA was 4 µM or 16 µM. These reaction mixtures were incubated for 10 minutes at 37° C. Then, 10 µL of ligand beacon resuspended in an appropriate binding buffer was added to the above reactions to a final concentration equivalent to the aptamer concentration. After 10 minutes further incubation at 37° C., fluorescence was measured. The results are depicted in FIGS. 9A–C, which demonstrates that ligand beacons can be successfully used with plasma.

Example 7

Cascade Hybridization The stem sequences of three stem-loop nucleic acids that will participate in a hybridization cascade are represented in FIG. 14A. The loop of stem-loop I comprises a sequence that is complementary to the target nucleic acid sequence that one would like to detect. Upon binding to the target nucleic acid, then stem of stem-loop I becomes dissociated (FIG. 14B). The arms of the dissociated stem then pair with those of stem-loop II and stem-loop III (FIG. 14C). The arms of stem-loops II and III can now pair with those of stem-loops III and II respectively (FIG. 14D). This pattern of hybridization between the stems of the three nucleic acids will continue bidirectionally until one of the stem-loops is depleted.

---

What is claimed is:

1. A method for detecting the presence or absence of a target molecule in a test mixture which may contain said target molecule comprising:
   a) contacting the test mixture with a first nucleic acid ligand which binds to said target molecule, wherein said first nucleic acid ligand undergoes a conformational change;
   b) contacting the mixture produced by step a) with a second nucleic acid ligand which binds to the conformationally changed first nucleic acid ligand, wherein said second nucleic acid ligand undergoes a conformational change;
   c) contacting the mixture produced by step b) with a third nucleic acid ligand which binds to the conformationally changed second nucleic acid ligand, thereby forming a cascade hybridization complex; and
   d) detecting the presence of said cascade hybridization complex.

2. The method of claim 1 wherein at least one of said nucleic acid ligands is labeled with at least one fluorescent group and at least one fluorescence modifying group, wherein the emission profile of said fluorescent group is different when said target molecule is present in the test mixture from when said target molecule is not present.

3. The method of claim 2 wherein said fluorescence modifying group is a quenching group.

4. The method of claim 2 wherein said cascade hybridization complex is detected by measuring the emission profile of said fluorescent group in the mixture produced in step c).

5. The method of claim 1 wherein said target-binding nucleic acid ligand is immobilized on the surface of a solid support prior to step a).

6. The method of claim 5 wherein said solid support is a biochip.

7. The method of claim 1 wherein a plurality of species of first nucleic acid ligands is attached to a solid suppport prior to step a), wherein each of said species of first nucleic acid ligands has a specific affinity for a different target molecule which may be contained in said test mixture, and wherein step a) is accomplished by contacting said solid support with a test mixture which may contain one or more of the target molecules to which the first nucleic acid ligands can bind.

8. A method for detecting the binding of an antibody to a target molecule comprising:
   a) conjugating said antibody to a first nucleic acid ligand;
   b) contacting a test mixture which may contain said target molecule with the antibody bound nucleic acid ligand, wherein said target molecule binds to said antibody bound nucleic acid ligand complex, wherein said first nucleic acid ligand undergoes a conformational change;
   c) contacting the mixture produced by step b) with a second nucleic acid ligand which binds to the conformationally changed first nucleic acid ligand, wherein said second nucleic acid ligand undergoes a conformational change;
   d) contacting the mixture produced by step c) with a third nucleic acid ligand which binds to the conformationally changed second nucleic acid ligand, thereby forming a cascade hybridization complex; and
   e) detecting the presence of said cascade hybridization complex.

9. The method of claim 8 wherein at least one of said nucleic acid ligands is labeled with at least one fluorescent group and at least one fluorescence modifying group, wherein the emission profile of said fluorescent group is different when said target molecule is present in the test mixture from when said target molecule is not present.

10. The method of claim 9 wherein said fluorescence modifying group is a quenching group.

* * * * *

SEQUENCE LISTING

<160> NUMBER OF SEQ ID NOS: 18

<210> SEQ ID NO 1
<211> LENGTH: 38
<212> TYPE: DNA
<213> ORGANISM: Artificial Sequence

```
<220> FEATURE:
<223> OTHER INFORMATION: Description of Artificial Sequence: Synthetic
      Sequence

<400> SEQUENCE: 1
tgggagggcg cgttcttcgt ggttactttt agtcccgt                           38

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(37)
<223> OTHER INFORMATION: G at position 1 substituted with
      5'-fluorescein; C at position 37 substituted with
      3'-(4-dimethylaminophenylazo)benzoic acid

<400> SEQUENCE: 2
gcgagaaagt aaccacgaag aagaacgcgc ccctcgc                            37

<210> SEQ ID NO 3
<211> LENGTH: 51
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 3
tggcggagcg atcatctcag agcattctta gcgttttgtt cttgtgtatg a            51

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(34)
<223> OTHER INFORMATION: G at position 1 is substituted with
      5'-fluorescein; C at position 34 is substituted with
      3'-(4-dimethylaminophenylazo)benzoic acid.

<400> SEQUENCE: 4
gcgagcaaga acaaaacgct aagaatgctc tcgc                               34

<210> SEQ ID NO 5
<211> LENGTH: 49
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 5
tagccaaggt aaccagtaca aggtgctaaa cgtaatggct tcggcttac               49

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
```

```
                              Sequence
<220> FEATURE:
<221> NAME/KEY: modified_base
<222> LOCATION: (1)..(30)
<223> OTHER INFORMATION: G at position 1 is substituted with
      5'-fluorescein; C at position 30 is substituted with
      3'-(4-dimethylaminophenylazo)benzoic acid.

<400> SEQUENCE: 6
gcgagtgtac tggttacctt ggctactcgc                                       30

<210> SEQ ID NO 7
<211> LENGTH: 38
<212> TYPE: RNA
<213> ORGANISM: Artificial Sequence
<220> FEATURE:
<223> OTHER INFORMATION: Description of Artificial Sequence:  Synthetic
      Sequence
<220> FEATURE:
<221> NAME/KEY: modified_base
<222> LOCATION: (1)..(38)
<223> OTHER INFORMATION: All pyrimidines are 2'-F.

<400> SEQUENCE: 7
cucaacgagc caggaacauc gaggucagca aacgcgag                              38

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:  Synthetic
      Sequence
<220> FEATURE:
<221> NAME/KEY: modified_base
<222> LOCATION: (1)..(30)
<223> OTHER INFORMATION: G at position 1 is substituted with
      5'-fluorescein; C at position 30 is substituted with
      3'-(4-dimethylaminophenylazo)benzoic acid.

<400> SEQUENCE: 8
gcgagctcgc gtttgctgac gtcgactcgc                                       30

<210> SEQ ID NO 9
<211> LENGTH: 64
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 9
ttggtctctg gcggagcgat catctcagag cattcttagc gttttgttct tgtgtatgat      60
tcgc                                                                   64

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 10
ttggagggcg cgttcttcgt ggttactttt agtccc                                36

<210> SEQ ID NO 11
<211> LENGTH: 49
```

```
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 11
tagccaaggt aaccagtaca aggtgctaaa cgtaatggct tcggcttac              49

<210> SEQ ID NO 12
<211> LENGTH: 62
<212> TYPE: RNA
<213> ORGANISM: Artificial Sequence
<220> FEATURE:
<223> OTHER INFORMATION: Description of Artificial Sequence: Synthetic
      Sequence
<220> FEATURE:
<221> NAME/KEY: modified_base
<222> LOCATION: (1)..(62)
<223> OTHER INFORMATION: All pyrimidines are 2'-F.

<400> SEQUENCE: 12
gggagacaag aauaaacgcu caacgagcca ggaacaucga ggucagcaaa cgcgagcgcg   60
ag                                                                  62

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 13
aggctagcta                                                          10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 14
tagggagatt                                                          10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 15
aatctcccta                                                          10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      Sequence

<400> SEQUENCE: 16
```

-continued

```
tagtttgagg                                                          10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 17
cctcaaacta                                                          10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence:  Synthetic
      Sequence

<400> SEQUENCE: 18
tagctagcct                                                          10
```